United States Patent [19]
Diab et al.

[11] Patent Number: 6,067,462
[45] Date of Patent: May 23, 2000

[54] SIGNAL PROCESSING APPARATUS AND METHOD

[75] Inventors: Mohamed K. Diab; Rex McCarthy, both of Mission Viejo, Calif.

[73] Assignee: Masimo Corporation, Iryine, Calif.

[21] Appl. No.: 09/081,539

[22] Filed: May 19, 1998

Related U.S. Application Data

[62] Division of application No. 08/834,194, Apr. 14, 1997.
[51] Int. Cl.[7] ....................................................... A61B 5/00
[52] U.S. Cl. ........................... 600/310; 600/336; 600/481; 702/191
[58] Field of Search ..................................... 600/300, 310, 600/322, 323, 324, 336, 481, 508, 509, 515; 702/191–197

[56] References Cited

U.S. PATENT DOCUMENTS

| Re. 35,122 | 12/1995 | Corenman et al. . |
| 3,647,299 | 3/1972 | Lavallee . |

(List continued on next page.)

FOREIGN PATENT DOCUMENTS

| 0102816 | 3/1984 | European Pat. Off. . |
| 0329196 | 8/1989 | European Pat. Off. . |
| 0743042 | 11/1996 | European Pat. Off. . |
| 0744154 | 11/1996 | European Pat. Off. . |
| WO9409698 | 5/1994 | WIPO . |

OTHER PUBLICATIONS

Haykin, Simon, Adaptive Filter Theory, Prentice Hall, Englewood Cliffs, NJ, Chapter 9, "Recursive Least–Squares Lattice Filters," pp. 451–493, 1985.
Widrow, Bernard, Adaptive Signal Processing, Prentice Hall, Englewood Cliffs, NJ, Chapter 1, "Adaptive Systems," pp. 3–13, 1985.
Widrow, Bernard et al., Chapter 2: "The Adaptive Linear Combiner", Adaptive Signal Processing, Prentice–Hall, Inc., pp. 15–26, 1985.
Widrow, Bernard et al., Chapter 12: "Adaptive Interference Canceling", Adaptive Signal Processing, Prentice–Hall, Inc., pp. 302–367., 1985.
Widrow, Bernard et al., Chapter 2: "The Adaptive Linear Combiner", Adaptive Signal Processing, Prentice–Hall, Inc., pp. 15–26.
Tremper, Kevin K. et al., "Pulse Oximetry: Technical Aspects of Machine Design" by Jonas A. Pologe, *Advances in Oxygen Monitoring*, Little, Brown and Company, 1987, pp. 137–153.
Klimasauskas, Casey, "Neural Nets and Noise Filtering" Article, Dr. Dobb's Journal, Jan. 1989, pp. 32–34, 36–38, 42, 47, 49, 96, 98,100.

(List continued on next page.)

*Primary Examiner*—Eric F. Winakur
*Attorney, Agent, or Firm*—Knobbe, Martens, Olson & Bear, LLP

[57] ABSTRACT

A method and an apparatus to analyze two measured signals that are modeled as containing desired and undesired portions such as noise, FM and AM modulation. Coefficients relate the two signals according to a model defined in accordance with the present invention. In one embodiment, a transformation is used to evaluate a ratio of the two measured signals in order to find appropriate coefficients. The measured signals are then fed into a signal scrubber which uses the coefficients to remove the unwanted portions. The signal scrubbing is performed in either the time domain or in the frequency domain. The method and apparatus are particularly advantageous to blood oximetry and pulserate measurements. In another embodiment, an estimate of the pulserate is obtained by applying a set of rules to a spectral transform of the scrubbed signal. In another embodiment, an estimate of the pulserate is obtained by transforming the scrubbed signal from a first spectral domain into a second spectral domain. The pulserate is found by identifying the largest spectral peak in the second spectral domain.

14 Claims, 19 Drawing Sheets

U.S. PATENT DOCUMENTS

| | | |
|---|---|---|
| 3,704,706 | 12/1972 | Herczfeld et al. . |
| 4,063,551 | 12/1977 | Sweeney . |
| 4,086,915 | 5/1978 | Kofsky et al. . |
| 4,095,117 | 6/1978 | Nagy . |
| 4,129,124 | 12/1978 | Thalman . |
| 4,308,456 | 12/1981 | Van Der Gaag et al. . |
| 4,407,290 | 10/1983 | Wilber . |
| 4,537,200 | 8/1985 | Widrow . |
| 4,649,505 | 3/1987 | Zinser, Jr. et al. . |
| 4,660,151 | 4/1987 | Chipman et al. . |
| 4,773,422 | 9/1988 | Isaacson et al. . |
| 4,793,361 | 12/1988 | DuFault . |
| 4,799,493 | 1/1989 | DuFault . |
| 4,800,495 | 1/1989 | Smith . |
| 4,802,486 | 2/1989 | Goodman et al. . |
| 4,824,242 | 4/1989 | Frick et al. . |
| 4,846,183 | 7/1989 | Martin . |
| 4,848,901 | 7/1989 | Hood, Jr. . |
| 4,854,699 | 8/1989 | Edgar, Jr. . |
| 4,859,057 | 8/1989 | Taylor et al. . |
| 4,860,759 | 8/1989 | Kahn et al. . |
| 4,863,265 | 9/1989 | Flower et al. . |
| 4,867,571 | 9/1989 | Frick et al. . |
| 4,869,253 | 9/1989 | Craig, Jr. et al. . |
| 4,869,254 | 9/1989 | Stone et al. . |
| 4,883,353 | 11/1989 | Hausman et al. . |
| 4,892,101 | 1/1990 | Cheung et al. . |
| 4,907,594 | 3/1990 | Muz . |
| 4,911,167 | 3/1990 | Coreman et al. . |
| 4,927,264 | 5/1990 | Shiga et al. . |
| 4,928,692 | 5/1990 | Goodman et al. . |
| 4,934,372 | 6/1990 | Corenman et al. . |
| 4,948,248 | 8/1990 | Lehman . |
| 4,955,379 | 9/1990 | Hall . |
| 4,956,867 | 9/1990 | Zurek et al. . |
| 5,003,977 | 4/1991 | Suzuki et al. . |
| 5,057,695 | 10/1991 | Hirao et al. . |
| 5,190,047 | 3/1993 | Odagiri et al. . |
| 5,273,036 | 12/1993 | Kronberg et al. . |
| 5,297,548 | 3/1994 | Pologe . |
| 5,308,919 | 5/1994 | Minnich . |
| 5,349,952 | 9/1994 | McCarthy et al. . |
| 5,398,680 | 3/1995 | Polson et al. . |
| 5,458,128 | 10/1995 | Polanyi et al. . |
| 5,490,505 | 2/1996 | Diab et al. . |
| 5,515,169 | 5/1996 | Cargill et al. . |
| 5,588,427 | 12/1996 | Tien . |
| 5,632,272 | 5/1997 | Diab et al. . |
| 5,704,365 | 1/1998 | Albrecht et al. .................. 600/515 |
| 5,738,104 | 4/1998 | Lo et al. . |

OTHER PUBLICATIONS

Neuman, Michael R., "Pulse Oximetry: Physical Principles, Technical Realization and Present Limitations", *Continous Transcutaneous Monitoring*, Plenum Press, New York, 1987, pp.135–144.

Severinghaus, John W. M.D., "Pulse Oximetry Uses and Limitations", ASA Convention 1989, New Orleans.

Cohen, Arnon Ph.D., "Volume I : Time and Frequency Domains Analysis", *Biomedical Signal Processing*, CRC Press, Inc., pp. 152–159.

Harris, Fred et al., "Digital Signal Processing With Efficient Polyphase Recursive All–Pass Filters" Article, Presented at International Conference on Signal Processing Florence, Italy, Sep. 4–6, 1991.

Rabiner, Lawrence R. et al., "Theory and Approximation of Infinite Impulse Response Digital Filters", Prentice Hall Inc., Englewood Cliffs, NJ, 1975, p. 260.

Mook, G.A. et al., "Spectrophotometric determination of oxygen saturation of blood independent of the presence of indocyanine green", *Cardiovascular Research*, vol. 13, 1979, pp. 233–237.

Melnikof, Steve, "Neural Networks for Signal Processing: A Case Study" Article, Dr. Dobb's Journal. Jan. 1989, pp. 36–37.

Mook, G.A. et al., "Wavelength dependency of the spectrophotometric determination of blood oxygen saturation", *Clinical Chemistry Acta*, vol. 26, 1969, pp. 170–173.

Brown, David P., "Evaluation of Pulse Oximeters using Theoretical Models and Experimental Studies" Masters Thesis, University of Washington, 1987.

SIGNAL PROCESSING APPARATUS AND METHOD

RELATED CASES

This application is a divisional of application Ser. No. 08/834,194, filed Apr. 14, 1997.

BACKGROUND OF THE INVENTION

1. Field of the Invention

The present invention relates to the field of signal processing. More specifically, the present invention relates to the processing of measured signals, containing a primary signal portion and a secondary signal portion, for the removal or derivation of either the primary or secondary signal portion when little is known about either of these components. The present invention is especially useful for physiological monitoring systems including blood oxygen saturation systems and pulserate measurement systems. The present invention further relates to a method and apparatus for signal processing of signals in order to compute an estimate for pulserate.

2. Description of the Related Art

Signal processors are typically employed to remove or derive either the primary or secondary signal portion from a composite measured signal including a primary signal portion and a secondary signal portion. For example, a composite signal may contain a primary signal portion comprising desirable data and a secondary signal portion comprising noise. If the secondary signal portion occupies a different frequency spectrum than the primary signal portion, then conventional filtering techniques such as low pass, band pass, and high pass filtering are available to remove or derive either the primary or the secondary signal portion from the total signal. Fixed single or multiple notch filters could also be employed if at least one of the primary and secondary signal portions exists at a fixed frequency band.

It is often the case that an overlap in frequency spectrum between the primary and secondary signal portions exists. Complicating matters further, the statistical properties of one or both of the primary and secondary signal portions may change with time. In such cases, conventional filtering techniques are ineffective in extracting either the primary or secondary signal. If, however, a description of either the primary or secondary signal portion can be derived, correlation canceling, such as adaptive noise canceling, can be employed to remove either the primary or secondary signal portion of the signal isolating the other portion. In other words, given sufficient information about one of the signal portions, that signal portion can be extracted.

Conventional correlation cancelers, such as adaptive noise cancelers, dynamically change their transfer function to adapt to and remove portions of a composite signal. However, correlation cancelers and adaptive noise cancelers require either a secondary reference or a primary reference which correlates to either the secondary signal portion only or the primary signal portion only. For instance, for a measured signal containing noise and desirable signal, the noise can be removed with a correlation canceler if a noise reference is available. This is often the case. Although the amplitudes of the reference signals are not necessarily the same as the amplitudes of the corresponding primary or secondary signal portions, the reference signals have a frequency spectrum which is similar to that of the primary or secondary signal portions.

In many cases, nothing or very little is known about the secondary and primary signal portions. One area where measured signals comprising a primary signal portion and a secondary signal portion about which no information can easily be determined is physiological monitoring. Physiological monitoring generally involves measured signals derived from a physiological system, such as the human body. Measurements which are typically taken with physiological monitoring systems include electrocardiographs, blood pressure, blood gas saturation (such as oxygen saturation), capnographs, other blood constituent monitoring, heart rate, respiration rate, electroencephalograph (EEG) and depth of anesthesia, for example. Other types of measurements include those which measure the pressure and quantity of a substance within the body such as cardiac output, venous oxygen saturation, arterial oxygen saturation, bilirubin, total hemoglobin, breathalyzer testing, drug testing, cholesterol testing, glucose testing, and carbon dioxide testing, protein testing, carbon monoxide testing, and other in-vivo measurements, for example. Complications arising in these measurements are often due to motion of the patient, both external and internal (muscle movement, vessel movement, and probe movement, for example), during the measurement process.

Many types of physiological measurements can be made by using the known properties of energy attenuation as a selected form of energy passes through a test medium such as a finger, shown schematically in FIG. 1.

A blood gas monitor is one example of a physiological monitoring system which is based upon the measurement of energy attenuated by biological tissues or substances. Blood gas monitors transmit light into the test medium and measure the attenuation of the light as a function of time. The output signal of a blood gas monitor which is sensitive to the arterial blood flow contains a component having a waveform representative of the patient's arterial pulse. This type of signal, which contains a component related to the patient's pulse, is called a plethysmographic wave, and is shown in FIG. 2A as a curve s(t) 201. Plethysmographic waveforms are used in blood gas saturation measurements. As the heart beats, the amount of blood in the arteries increases and decreases, causing increases and decreases in energy attenuation, illustrated by a cyclic wave seen in the curve 201.

Typically, a digit such as a finger, an ear lobe, or other portion of the body where blood flows close to the skin, is employed as the medium through which light energy is transmitted for blood gas attenuation measurements. The finger comprises skin, fat, bone, muscle, etc., as shown FIG. 1, each of which attenuates energy incident on the finger in a generally predictable and constant manner. However, when fleshy portions of the finger are compressed erratically, for example by motion of the finger, energy attenuation becomes erratic.

An example of a more realistic measured waveform is shown in FIG. 2B, as a curve M(t) 202. The curve 202 illustrates the effect of motion and noise n(t) added to the clean waveform s(t) shown in FIG. 201. The primary plethysmographic waveform portion of the signal M(t) is the waveform representative of the pulse, corresponding to the sawtooth-like pattern wave in curve 201. The large, secondary motion-induced excursions in signal amplitude obscure the primary plethysmographic signal s(t). Even small variations in amplitude make it difficult to distinguish the primary signal component s(t) in the presence of a secondary signal component n(t).

A pulse oximeter is a type of blood gas monitor which non-invasively measures the arterial saturation of oxygen in the blood. The pumping of the heart forces freshly oxygenated blood into the arteries causing greater energy attenuation. As well understood in the art, the arterial saturation of oxygenated blood may be determined from the depth of the valleys relative to the peaks of two plethysmographic waveforms measured at separate wavelengths. Patient movement introduces motion artifacts to the composite signal as illustrated in the plethysmographic waveform illustrated in FIG. 2B. These motion artifacts distort the measured signal.

SUMMARY OF THE INVENTION

The present invention involves several different embodiments using the novel signal model in accordance with the present invention to estimate the desired signal portion of a measured data signal where the measured data contains desired and undesired components. In one embodiment, a signal processor acquires a first measured signal and a second measured signal. The first signal comprises a desired signal portion and an undesired signal portion. The second measured signal comprises a desired signal portion and an undesired signal portion. The signals may be acquired by propagating energy through a medium and measuring an attenuated signal after transmission or reflection. Alternatively, the signals may be acquired by measuring energy generated by the medium.

In one embodiment, the desired signal portions of the first and second measured signals are approximately equal to one another, to within a first constant multiplier. The undesired signal portions of the first and second measured signals are also approximately equal to one another, to within a second constant multiplier. A scrubber coefficient may be determined, such that an estimate for the first signal can be generated by inputting the first and second measured signals, and the scrubber coefficient into a waveform scrubber. The output of the waveform scrubber is generated by multiplying the first measured signal by the scrubber coefficient and then adding the result to the second measured signal.

In one embodiment, the scrubber coefficient is determined by normalizing the first and second measured signals, and then transforming the normalized signals into a spectral domain. The spectral domain signals are then divided by one another to produce a series of spectral ratio lines. The need for waveform scrubbing can be determined by comparing the largest ratio line to the smallest ratio line. If the difference does not exceed a threshold value, the no scrubbing is needed. If the difference does exceed a threshold value, then the waveform must be scrubbed, and the scrubbing coefficient corresponds to the magnitude of the largest ratio line.

Another aspect of the present invention involves a physiological monitor having a signal processor which computes an estimate for an unknown pulserate from the measured data. In one embodiment, the signal processor receives measured data from a detector that measures a physiological property related to the heartbeat. The signal processor transforms the data into a spectral domain and then identifies a series of spectral peaks and the frequencies associated with those peaks. The signal processor then applies a set of rules to the spectral peaks and the associated frequencies in order to compute an estimate for the pulserate.

In yet another embodiment of the pulserate detector, the signal processor performs a first transform to transform the measured data into a first transform space. The signal processor then performs a second transform to transform the data from the first transform space into a second transform space. The signal processor then searches the data in the second transform space to find the pulserate.

In another embodiment, the transform into the first transform space is a spectral transform such as a Fourier transform. In another embodiment, the transform into the second transform space is a spectral transform such as a Fourier transform. In yet another embodiment, once the data has been transformed into the second transform space, the signal processor performs a 1/x mapping on the spectral coordinates before searching for the pulserate.

In another embodiment, the signal processor transforms the measured data into a first spectral domain, and then transforms the data from the first spectral domain into a second spectral domain. After twice transforming the data, the signal processor performs a 1/x remapping on the coordinates of the second spectral domain. The signal processor then searches the remapped data for the largest spectral peak corresponding to a pulserate less than 120 beats per minute. If such a peak is found, then the signal processor outputs the frequency corresponding to that peak as being the pulserate. Otherwise, the signal processor searches the data transformed into the first spectral domain for the largest spectral peak in that domain, and outputs a pulserate corresponding to the frequency of the largest peak in the first spectral domain.

In another embodiment of the pulserate detector, the signal processor first transforms the measured data into a first spectral domain. Then the signal processor takes the magnitude of the transformed data and then transforms the magnitudes into a second spectral domain. Then the signal processor then performs a 1/x mapping of the spectral coordinates. After the 1/x mapping, the signal processor feeds the transformed and remapped data into a neural network. The output of the neural network is the pulserate.

DETAILED DESCRIPTION OF THE DRAWINGS

Figure 1:
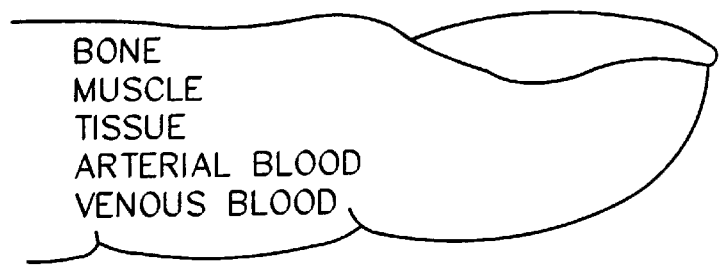
FIG. 1 schematically illustrates a typical finger.
Figure 2A:
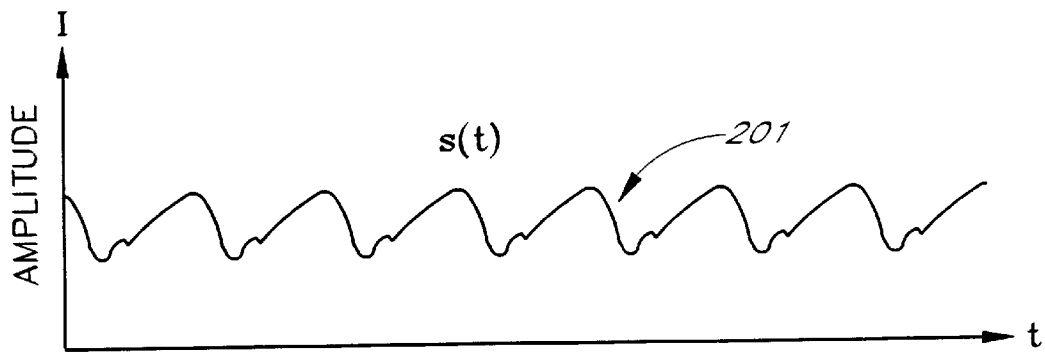
FIG. 2A illustrates an ideal plethysmographic waveform.
Figure 2B:
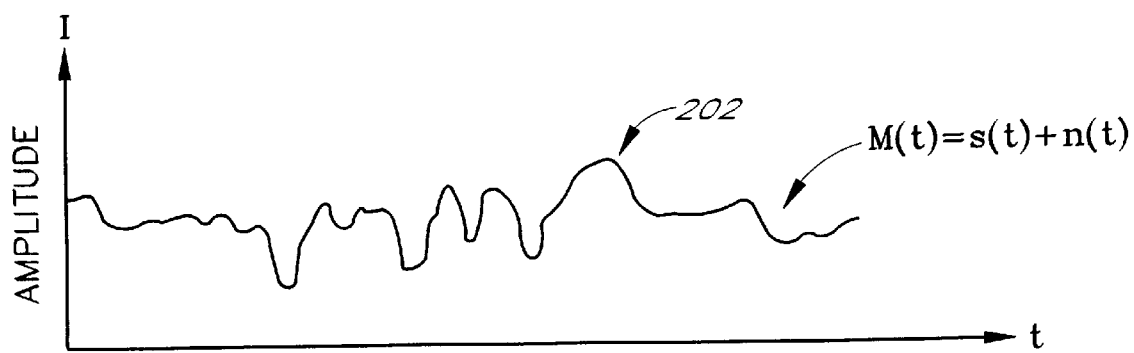
FIG. 2B illustrates a plethysmographic waveform which includes a motion-induced erratic signal portion.

The present invention involves a system which uses first and second measured signals that each contain a primary signal portion and a secondary signal portion In other words, given first and second composite signals $c_1(t)=s_1(t)+n_1(t)$ and $c_2(t)=s_2(t)+n_2(t)$, the system of the present invention can be used to isolate either the primary signal portion s(t) or the secondary signal portion n(t) of the two composite signals. Following processing, the output of the system provides a good approximation n"(t) to the secondary signal portion n(t) or a good approximation s"(t) to the primary signal portion s(t).

The system of the present invention is particularly useful where the primary signal portion s(t), the secondary signal portion n(t), or both, may contain one or more of a constant portion, a predictable portion, an erratic portion, a random portion, etc. The primary signal approximation s"(t) or the secondary signal approximation n"(t) is derived by removing as many of the secondary signal portions n(t) or primary signal portions s(t) from the composite signal c(t) as possible. The remaining signal forms either the primary signal approximation s"(t) or the secondary signal approximation n"(t), respectively. The constant portion and the predictable portion of the secondary signal n(t) are easily removed with traditional filtering techniques, such as simple subtraction, low pass, band pass, and high pass filtering. The erratic portion is more difficult to remove due to its unpredictable nature. If something is known about the erratic signal, even statistically, it could be removed, at least partially, from the measured signal via traditional filtering techniques. However, often no information is known about the erratic portion of the secondary signal n(t). In this case, traditional filtering techniques are usually insufficient.

In order to remove the secondary signal n(t), a signal model in accordance with the present invention is defined as follows for the first and second measured signals $c_1$ and $c_2$:

$$c_1 = s_1 + n_1 \qquad (1)$$

$$c_2 = s_2 + n_2 \quad \text{with} \qquad (2)$$

$$s_1 = r_a s_2 \text{ and } n_1 = r_v n_2 \text{ or} \qquad (3)$$

$$r_a = \frac{s_1}{s_2} \text{ and } r_v = \frac{n_1}{n_2} \qquad (4)$$

where $s_1$ and $n_1$ are at least somewhat (preferably substantially) uncorrelated and $S_2$ and $n_2$ are at least somewhat (preferably substantially) uncorrelated. The first and second measured signals $c_1$ and $c_2$ are related by correlation coefficients $r_a$ and $r_v$ as defined above. The use and selection of these coefficients is described in further detail below.

In accordance with one aspect of the present invention, this signal model is used in combination with a waveform scrubber to remove the undesired portion of the measured signals.

The description that follows can best be understood in view of the following list which briefly describes how the invention is broken down and described according to the following topics:

1. A general overview of pulse oximetry measurements, in connection with FIGS. 1 through 4, provides a general theory and system block diagram for a red/infrared pulse oximetry apparatus for measurement of physiological data such as blood oxygen saturation and pulserate;

2. A more detailed description of the relationship between the data RD(t) measured using red light, and the data IR(t) measured using infrared light, normalization of RD(t) and IR(t), and the relationship of the normalized RD(t) and IR(t) to blood oxygen saturation, is provided in connection with FIGS. 5 through 8;

3. A mathematical model and description of the effect of motion artifacts on RD(t) and IR(t) and a method for detecting and removing the artifacts to create a clean spectrum $F(\omega)=RD(\omega)/IR(\omega)$, are provided in connection with FIGS. 10 through 13;

4. A mathematical model and a description of a rule based signal processing technique used by the pulse oximeter to determine pulserate, are provided in connection with FIGS. 14 through 16; and 5. A mathematical model and a description of a transform based signal processing technique used by the pulse oximeter to determine pulserate, are provided in connection with FIG. 17.

PULSE OXIMETRY MEASUREMENTS

A specific example of a physiological monitor using a processor of the present invention to determine a secondary reference n'(t) for input to a canceler that removes erratic motion-induced secondary signal portions is a pulse oximeter. Pulse oximetry may also be performed using a processor of the present invention to determine a primary signal reference s'(t) which may be used for display purposes or for input to a processor to derive information about patient movement, pulserate, and venous blood oxygen saturation.

A pulse oximeter typically causes energy to propagate through a medium where blood flows close to the surface, for example, an ear lobe, or a digit such as a finger, a forehead or a fetus' scalp. An attenuated signal is measured after propagation through or reflected from the medium. The pulse oximeter estimates the saturation of oxygenated blood.

Freshly oxygenated blood is pumped at high pressure from the heart into the arteries for use by the body. The volume of blood in the arteries and arterioles varies with the heartbeat, giving rise to a variation in absorption of energy at the rate of the heartbeat, or the pulse. The blood scatters both red and infrared light, and thus as the volume of blood changes, the amount of scattering changes as well. Typically the effects due to scattering are small when compared to the effects due to the change in blood volume.

Oxygen depleted, or deoxygenated, blood is returned to the heart by the veins along with unused oxygenated blood. The volume of blood in the veins varies with back pressure due to breathing as well as local uncontrolled motion of muscles. These variations typically occur at a rate that is much slower than the heartbeat. Thus, when there is no motion induced variation in the thickness of the veins, venous blood causes a low frequency variation in absorption of energy. When there is motion induced variation in the thickness of the veins, the scattering changes as well and this absorption is coupled with the erratic variation in absorption due to motion artifacts.

In absorption measurements using the transmission of energy through a medium, two light emitting diodes (LEDs) are positioned close to a portion of the body where blood flows close to the surface, such as a finger, and a photodetector is positioned near the LEDs. Typically, in pulse oximetry measurements, one LED emits a visible wavelength, preferably red, and the other LED emits an infrared wavelength. However, one skilled in the art will realize that other wavelength combinations, as well as combinations of more than two wavelengths, could be used. The finger comprises skin, tissue, muscle, both arterial blood and venous blood, fat, etc., each of which absorbs light energy differently due to different absorption coefficients, different concentrations, different thicknesses, and changing optical pathlengths. When the patient is not moving, absorption is substantially constant except for the flow of blood. The constant attenuation can be determined and subtracted from the signal via traditional filtering techniques. When the patient moves, this causes perturbation such as changing optical pathlength due to movement of background fluids (e.g., venous blood having a different saturation than the arterial blood). Therefore, the measured signal becomes erratic. Erratic motion induced noise typically cannot be predetermined and/or subtracted from the measured signal via traditional filtering techniques. Thus, determining the oxygen saturation of arterial blood and venous blood becomes more difficult.

Figure 3:
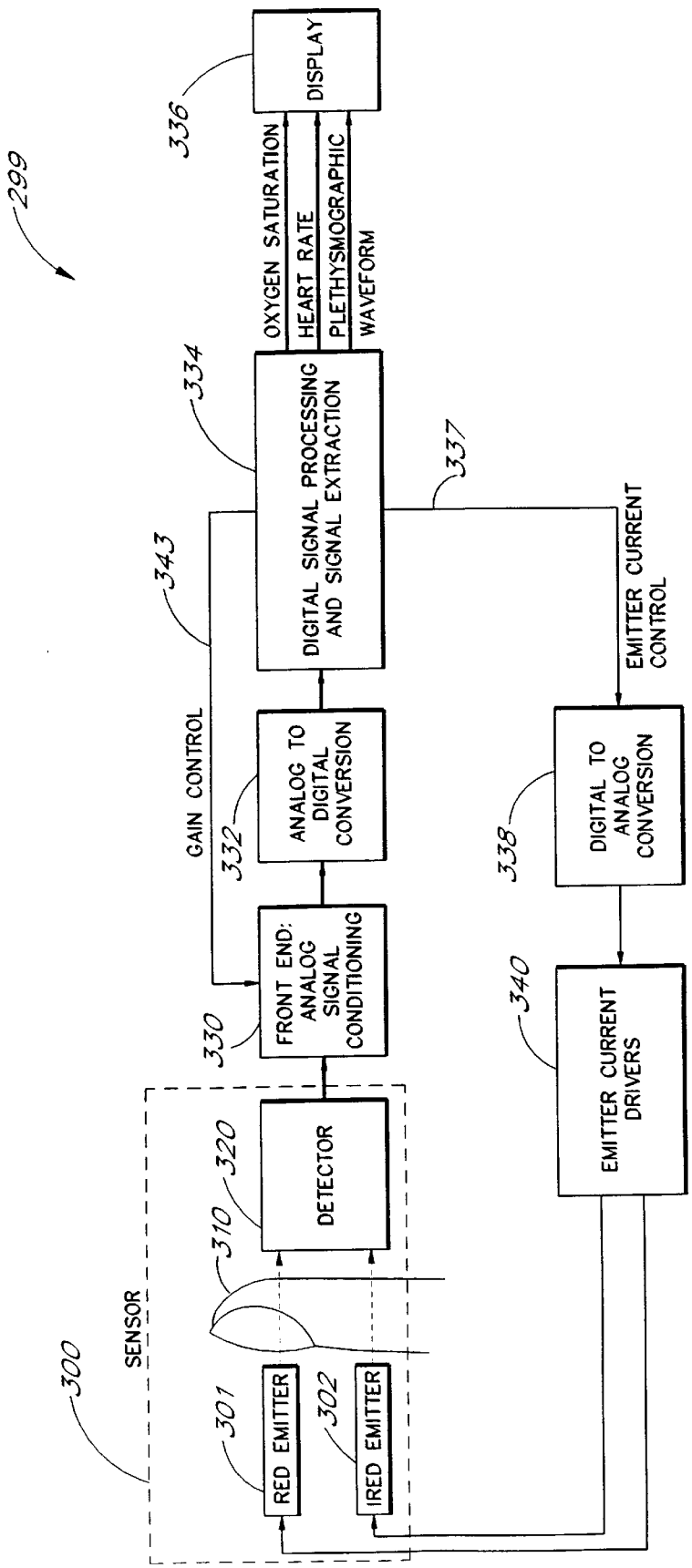
FIG. 3 illustrates a schematic diagram of a physiological monitor in accordance with the teachings of one aspect of the present invention

FIG. 3 depicts a general hardware block diagram of a pulse oximeter 299. A sensor 300 has two light emitters 301 and 302, such as LED's. One LED 301 emitting light of red wavelengths and another LED 302 emitting light of infrared wavelengths are placed adjacent a finger 310. A photodetector 320, which produces an electrical signal corresponding to the attenuated visible and infrared light energy signals is, located near the LED's 301 and 302. The photodetector 320 is connected to front end analog signal conditioning circuitry 330.

The front end analog signal conditioning circuit 330 has outputs coupled to an analog to digital conversion circuit 332. The analog to digital conversion circuit 332 has outputs coupled to a digital signal processing system 334. The digital signal processing system provides the desired parameters as outputs for a display 336. Outputs for display are, for example, blood oxygen saturation, heart rate, and a clean plethysmographic waveform.

The signal processing system also provides an emitter current control output 337 to a digital-to-analog converter circuit 338 which provides control information for a set of light emitter drivers 340. The light emitter drivers 340 couple to the light emitters 301, 302. The digital signal processing system also provides a gain control output 343 for the front end analog signal conditioning circuitry 330.

Figure 4:
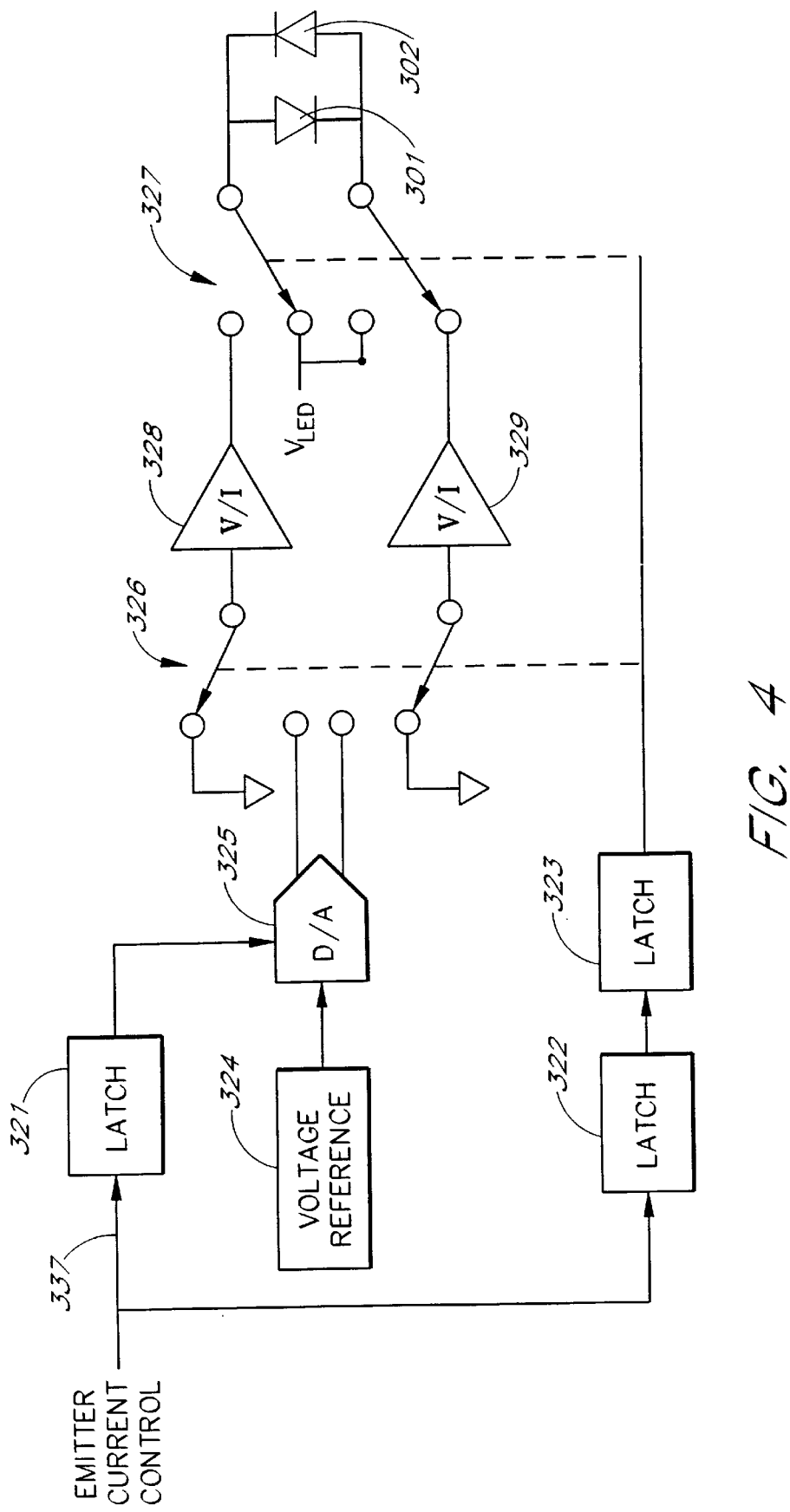
FIG. 4 illustrates an example of a low noise emitter current driver with accompanying digital to analog converter in accordance with the teachings of one aspect of the present invention.

FIG. 4 illustrates a preferred embodiment for the combination of the emitter drivers 340 and the digital to analog conversion circuit 338. As depicted in FIG. 4, the driver comprises first and second input latches 321, 322, a synchronizing latch 323, a voltage reference 324, a digital to analog conversion circuit 325, first and second switch banks 326, 327, first and second voltage to current converters 328, 329 and the LED emitters 301, 302 corresponding to the LED emitters 301, 302 of FIG. 3.

The preferred driver depicted in FIG. 4 is advantageous in that the present inventors recognized that much of the noise in the oximeter 299 of FIG. 3 is caused by the LED emitters 301, 302. Therefore, the emitter driver circuit of FIG. 4 is designed to minimize the noise from the emitters 301, 302. The first and second input latches 321, 322 are connected directly to the digital signal processor (DSP) bus 337. Therefore, these action of these latches significantly minimizes the bandwidth (resulting in noise) present on the DSP bus 337 which passes through to the driver circuitry of FIG. 4. The outputs of the first and second input latches 321, 322, only change when the latches detect their respective address on the DSP bus 337. The first input latch 321, receives the setting for the digital to analog converter circuit 325. The second input latch 322 receives switching control data for the switch banks 326, 327. The synchronizing latch 323 accepts the synchronizing pulses which maintain synchronization between the activation of emitters 301, 302 and the analog to digital conversion circuit 332.

The voltage reference 324 is also chosen as a low noise DC voltage reference for the digital to analog conversion circuit 325. In addition, in the present embodiment, the voltage reference 324 has a lowpass output filter with a very low corner frequency (e.g., 1 Hz in the present embodiment). The digital to analog converter 325 also has a lowpass filter at its output with a very low corner frequency (e.g., 1 Hz). The digital to analog converter 338 provides signals for each of the emitters 301, 302.

In the present embodiment, the output of the voltage to current converters 328, 329 are switched such that with the emitters 301, 302 connected in back-to-back configuration, only one emitter is active an any given time. In addition, the voltage to current converter 328 or 329 for the inactive emitter is switched off at its input as well, such that it is completely deactivated. This reduces noise from the switching and voltage to current conversion circuitry. In the present embodiment, low noise voltage to current converters are selected (e.g., Op 27 Op Amps), and the feedback loop is configured to have a low pass filter to reduce noise. In the present embodiment, the low pass filtering function of the voltage to current converters 328, 329 has a corner frequency of just above 316.7 Hz, which is the switching speed for the emitters, as further discussed below. Accordingly, the preferred driver circuit of FIG. 4, minimizes the noise of the emitters 301, 302.

In general, each of the red and infrared light emitters 301, 302 emits energy which is partially absorbed by the finger 310 and the remaining energy is received by the photodetector 320. The photodetector 320 produces an electrical signal which corresponds to the intensity of the light energy striking the photodetector 320. The front end analog signal conditioning circuitry 330 receives the intensity signals and filters and conditions these signals, as further described below, for further processing. The resultant signals are provided to the analog-to-digital conversion circuitry 332 which converts the analog signals to digital signals for further processing by the digital signal processing system 334. In the present embodiment, the output of the digital signal processing system provides clean plethysmographic waveforms of the detected signals and provides values for oxygen saturation and pulse rate to the display 336.

It should be understood that in different embodiments of the present invention, one or more of the outputs may be provided. The digital signal processing system 334 also provides control for driving the light emitters 301, 302 with an emitter current control signal on the emitter current control output 337. This value is a digital value which is converted by the digital-to-analog conversion circuit 338 which provides a control signal to the emitter current drivers 340. The emitter current drivers 340 provide the appropriate current drives for the red emitter 301 and the infrared emitter 302. Further detail of the operation of the physiological monitor for pulse oximetry is explained below.

In the present embodiment, the light emitters 301, 302 are driven via the emitter current driver 340 to provide light transmission with digital modulation at 316.7 Hz. In the present embodiment, the light emitters 301, 302 are driven at a power level which provides an acceptable intensity for detection by the detector and for conditioning by the front end analog signal conditioning circuitry 330. Once this energy level is determined for a given patient by the digital signal processing system 334, the current level for the red and infrared emitters is maintained constant. It should be understood, however, that the current may be adjusted for changes in the ambient room light and other changes which would effect the voltage input to the front end analog signal conditioning circuitry 330. In the present invention, the red and infrared light emitters 301, 302 are modulated as follows: for one complete 316.7 Hz red cycle, the red emitter 301 is activated for the first quarter cycle, and off for the remaining three-quarters cycle; for one complete 316.7 Hz infrared cycle, the infrared light emitter 302 is activated for one quarter cycle and is off for the remaining three-quarters cycle. In order to only receive one signal at a time, the emitters are cycled on and off alternatively, in sequence, with each only active for a quarter cycle per 316.7 Hz cycle and with a quarter cycle separating the active times.

The light signal is attenuated (amplitude modulated) by the pumping of blood through the finger 310 (or other sample medium). The attenuated (amplitude modulated) signal is detected by the photodetector 320 at the 316.7 Hz carrier frequency for the red and infrared light. Because only a single photodetector is used, the photodetector 320 receives both the red and infrared signals to form a time division multiplexed (TDM) signal. The TDM signal is provided to the front analog signal conditioning circuitry 330 and may be demodulated by either before or after analog to digital conversion.

Saturation Curves and Normalization

Figure 5:
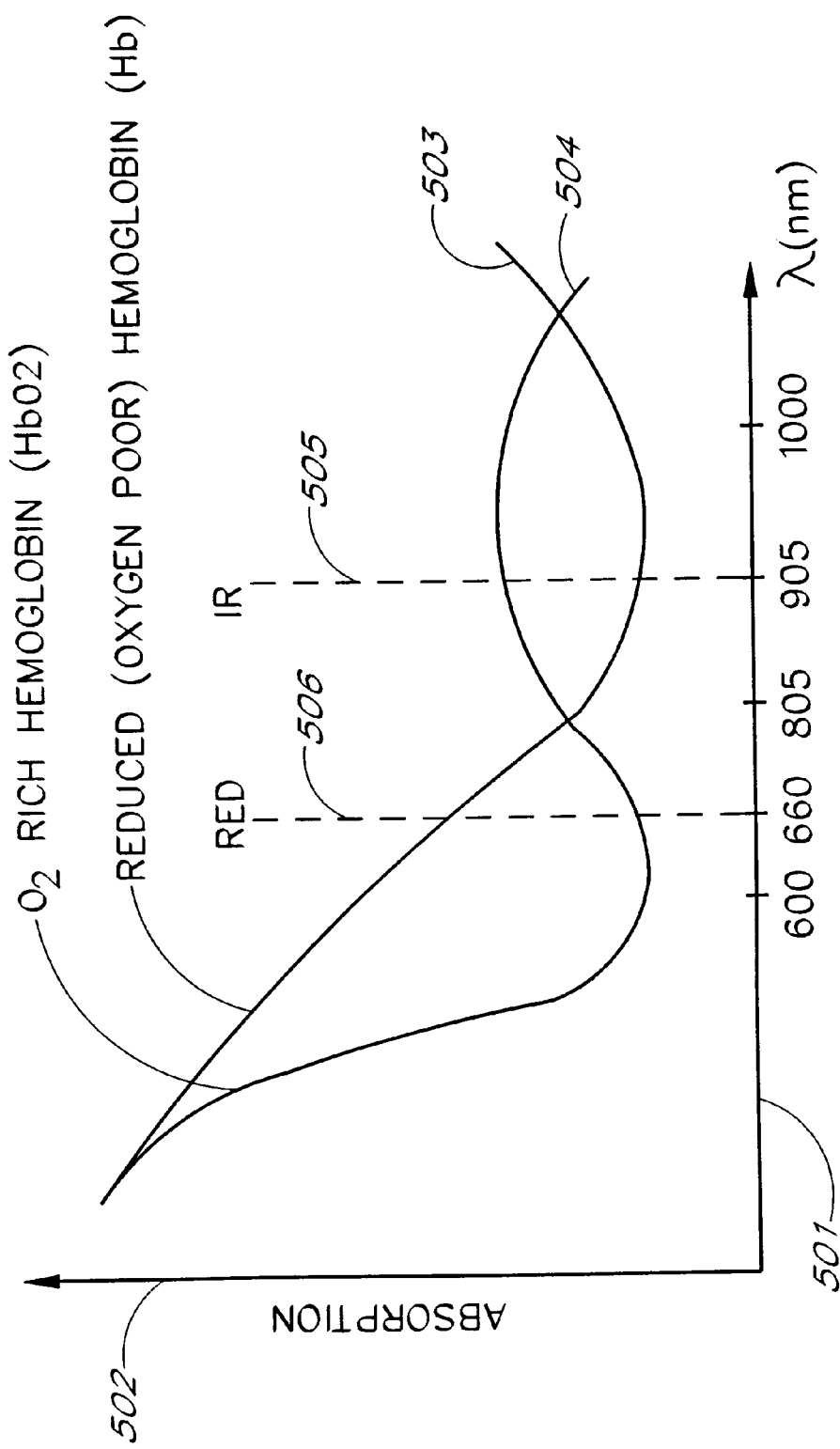
FIG. 5 illustrates the absorption properties of hemoglobin at various wavelength.

The ability of the apparatus 299 to measure the desired physiologic properties lies in the optical absorption properties of hemoglobin, as illustrated in FIG. 5. FIG. 5 shows an x axis 501 corresponding to a wavelength of light and a y axis 502 corresponding to an absorption coefficient for light passing through a medium. A reduced hemoglobin (Hb) curve 503 shows the absorption properties of oxygen poor hemoglobin. An oxygen rich hemoglobin (Hb02) curve 504 shows the absorption properties of oxygen rich hemoglobin. A reference line 506 highlights the region where the curves 503 and 504 pass through a value on the x axis 501 corresponding to 660 nm (nanometer) wavelength (the nominal operational wavelength of the red emitter 301). A reference line 505 highlights the region where the curves 503 and 504 pass through a value on the x axis 501 corresponding to 905 nm wavelength (the nominal operational wavelength of the infrared emitter 302).

At the reference line 506, the Hb curve 503 shows more absorption than the HbO2 curve 504. Conversely, at the reference line 505, the HbO2 curve shows more absorption than the Hb curve 503. The pulse oximeter can thus measure the blood oxygen saturation by measuring absorption of the blood at 660 nm and 905 nm, and the comparing the two absorption measurements.

According to the Beer-Lambert law of absorption, the intensity of light transmitted through an absorbing medium is given by:

$$I = I_0 e^{-\epsilon d c} \qquad (5)$$

where $I_0$ is the intensity of the incident light, $\epsilon$ is the absorption coefficient, c is the concentration coefficient and d is the thickness of the absorbing medium. In pulse oximetry applications, there are two sources, red and infrared, and thus two incident intensities, $I_{0,RD}$ for red, and $I_{0,IR}$ for infrared. Furthermore, in blood there are two concentrations of interest, namely the concentration of oxygen poor hemoglobin, denoted by $C_{Hb}$, and the concentration of oxygen rich hemoglobin, denoted by $C_{HbO2}$. The combination of the two optical wavelengths and the two concentrations means that there are four absorption coefficients, namely $\epsilon_{RD,Hb}$, $\epsilon_{RD,HbO2}$, $\epsilon_{IR,Hb}$, and $\epsilon_{IR,HbO2}$. Using these quantities, and assuming no time variation in any of the values except d, gives two separate Beer-Lambert equations for the pulse oximeter.

$$I_{RD} = I_{0,RD} e^{-[\epsilon_{RD,Hb} C_{Hb} + \epsilon_{RD,HbO2} C_{HbO2}] d(t)} \qquad (6)$$

$$I_{IR} = I_{0,IR} e^{-[\epsilon_{IR,Hb} C_{Hb} + \epsilon_{IR,HbO2} C_{HbO2}] d(t)} \qquad (7)$$

The measurement apparatus 299 does not provide a capability for measuring the incident terms $I_{0,RD}$ and $I_{0,IR}$ appearing in the above equation, and thus, strictly speaking, the value of $I_{RD}$ and $I_{IR}$ cannot be determined. However, in the pulse oximeter, only differential measurements are necessary. In other words, it is only the time varying nature of the values $I_{RD}$ and $I_{IR}$ and the relationship between the values that are important. The time variation in d(t) occurs primarily because blood flows in and out of the finger with each heartbeat. As blood flows into the finger, the effective value of d, as well as the scattering component, increases, and as blood flows out, the effective value of d and the scattering decreases. There are also time variations in the concentrations $C_{Hb}$ and $C_{HbO2}$ as the blood oxygen saturation level changes. Fortunately, these variations are slow compared to the variations in d(t), and they can be ignored.

Figure 6:
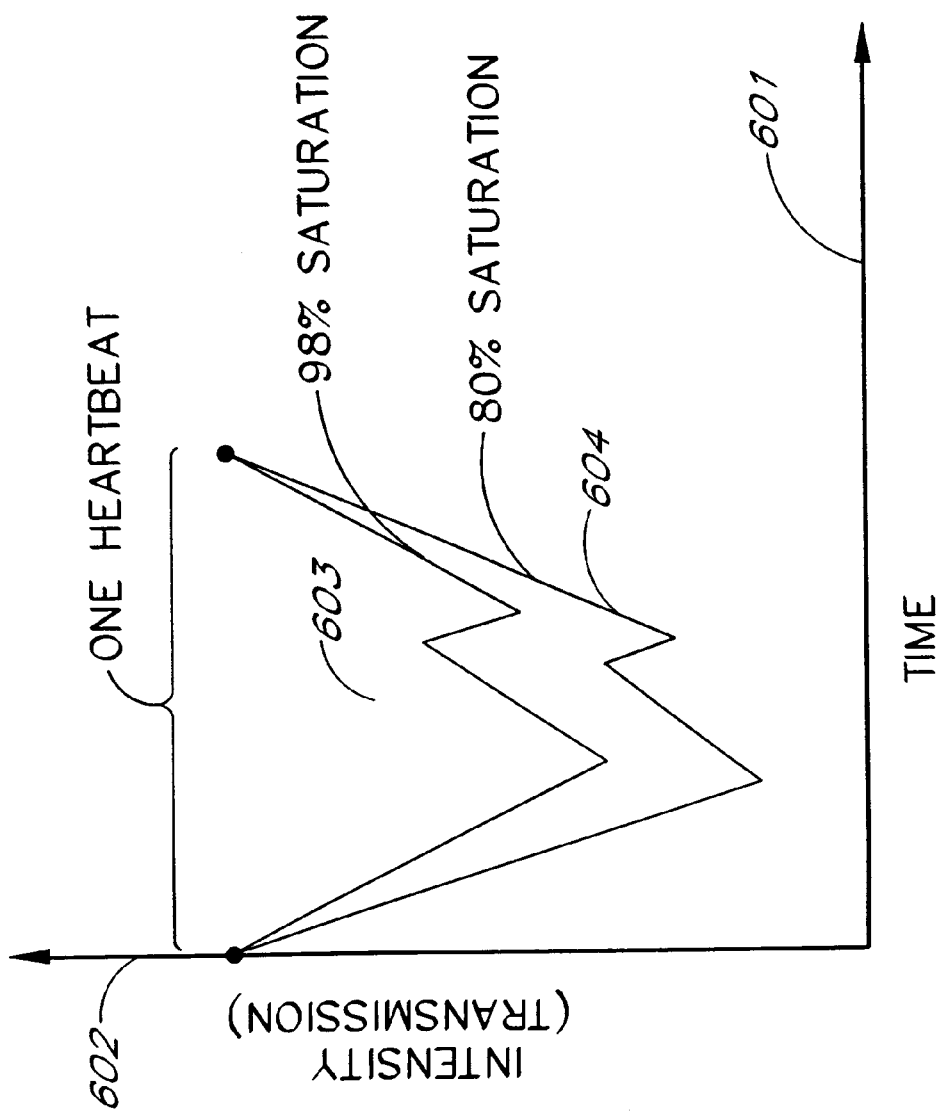
FIG. 6 illustrates one cycle of an idealized plethysmographic waveform for various levels of oxygen saturation at a fixed perfusion.

FIG. 6 illustrates one cycle of an idealized plethysmographic waveform for various levels of oxygen saturation. The figure shows an x-y plot having a time axis 601 in the x direction, and a transmission axis 602 in the y direction. The transmission axis 602 shows the intensity of the red light transmitted through the finger. A curve 604 shows the transmission of red light for 80% blood oxygen saturation. A curve 603 shows transmission of red light for 98% blood oxygen saturation. The curves 603 and 604 are intended to show different values of saturation given the same perfusion d. As shown in the figure, at the beginning of a heartbeat, red transmission is at a maximum because the finger contains relatively little blood. As the heartbeat progresses, blood is perfused into the finger and the amount of light transmission diminishes. Transmission diminishes because the additional material, the blood, increases the effective path length d in Equation (6). Transmission also diminishes somewhat because of scattering produced by the blood. If the blood is highly saturated with oxygen, as shown in the curve 603, the transmission diminishes only slightly because, as shown in FIG. 5, HbO2 has a relatively small absorption coefficient in the red wavelengths. If the blood has low oxygen saturation, as shown in the curve 604, then transmission diminishes significantly more because, as shown in FIG. 5, Hb has a relatively large absorption in the red wavelengths.

If FIG. 6 were redrawn to show the transmission properties of infrared light, then the curves 603 and 604 would essentially be interchanged, because as shown in FIG. 5, more infrared light is absorbed by HbO2 than is absorbed by Hb.

Figure 7:
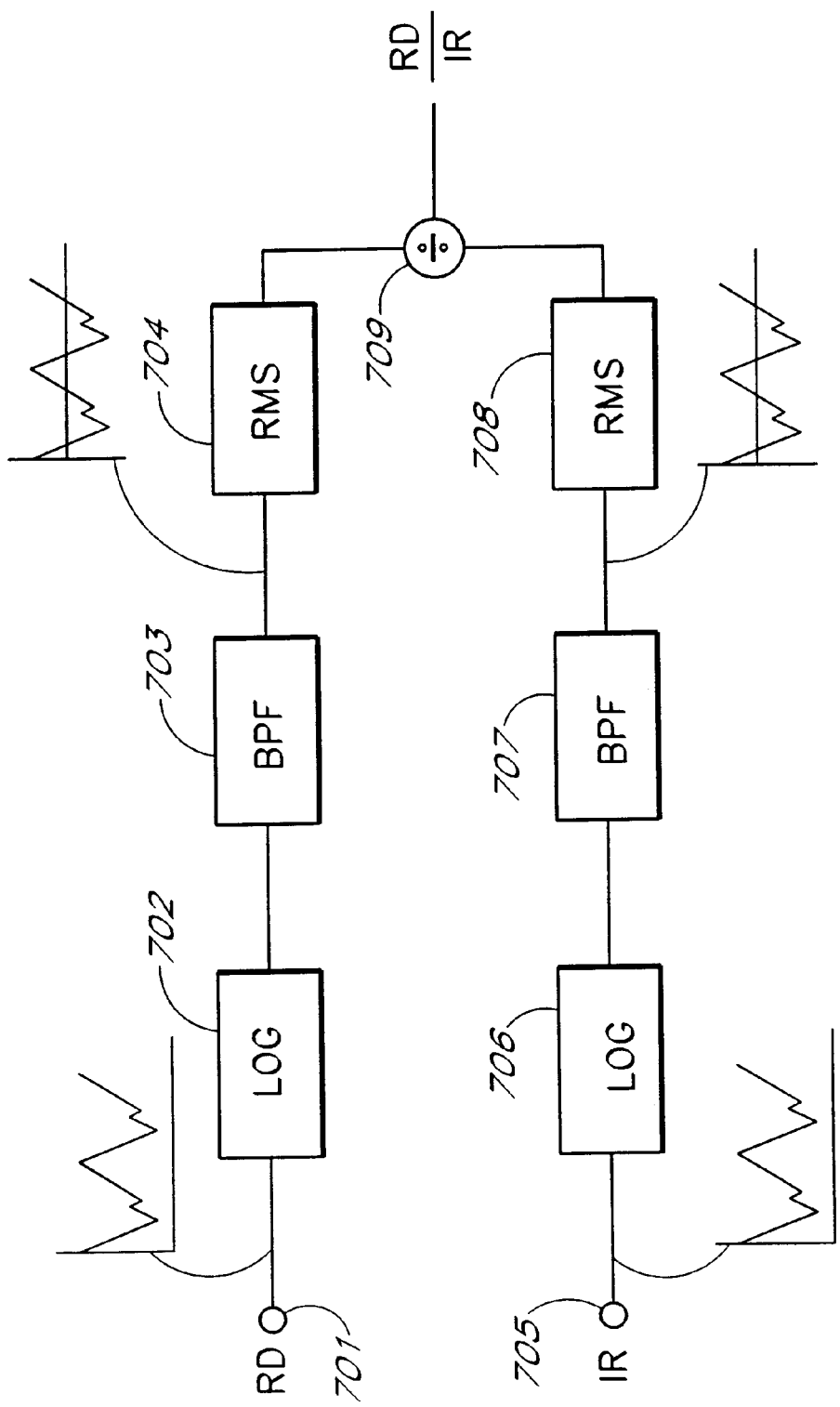
FIG. 7 illustrates a block diagram of the signal processing used to compute the ratio of red signal to infrared signal in accordance with one aspect of the present invention.

The above properties of the absorption of light by Hb and HbO2 advantageously provide a way to measure blood oxygen saturation by computing the ratio of red light to infrared light. FIG. 7 shows one embodiment of a signal processing apparatus for obtaining the desired ratio. FIG. 7 shows a red signal path which begins at a RD signal input 701. The RD signal input 701 corresponds to the amount of red light transmitted through the finger. The signal at the RD signal input 701 is fed into a logarithmic amplifier 702 which in turn feeds a bandpass filter 703. The output of the bandpass filter 703 is fed into a root-means-square (RMS) detector 704. The output of the RMS detector 704 is fed to a numerator input of a divider 709. FIG. 7 further shows an IR signal path comprising an IR input 705, a logarithmic amplifier 706, a bandpass filter 707, and an RMS detector 708. The output of the RMS detector 708 is fed to a denominator input of the divider 709.

In a preferred embodiment, the elements shown in FIG. 7 are part of the signal processing block shown in FIG. 3. The RD input 701 and IR input 705 are obtained by demultiplexing the output of the detector 320, also shown in FIG. 3. The signals at the inputs 701 and 705 correspond to $I_{RD}$ and $I_{IR}$ respectively, and are similar to the curves shown in FIG. 6. However, in the preferred embodiment, the signals are uncalibrated (i.e., the scale of the y axis 602 is unknown) because the value of $I_{O,RD}$ and $I_{O,IR}$ in Equations (6) and (7) are unknown. This is not an impediment to the measurement of the blood oxygen saturation, because saturation can be obtained without reference to either $I_{O,RD}$ or $I_{O,IR}$ as follows. Taking the natural logarithm (in signal processing blocks 702 and 706) of both Equation (6) and Equation (7) yields:

$$\ln(I_{RD}) = \ln(I_{0,RD}) - [\epsilon_{RD,Hb}C_{Hb} + \epsilon_{RD,HbO2}C_{HbO2}]d(t) \quad (8)$$

$$\ln(I_{IR}) = \ln(I_{0,IR}) - [\epsilon_{IR,Hb}C_{Hb} + \epsilon_{IR,HbO2}C_{HbO2}]d(t) \quad (9)$$

Applying a bandpass filter (in signal processing blocks 703 and 707) removes the non-time varying components, and allows Equations (8) and (9) to be rewritten as:

$$RD(t) = -[\epsilon_{RD,Hb}C_{Hb} + \epsilon_{RD,HbO2}C_{HbO2}]d(t) \quad (10)$$

$$IR(t) = -[\epsilon_{IR,Hb}C_{Hb} + \epsilon_{IR,HbO2}C_{HbO2}]d(t) \quad (11)$$

Figure 8:
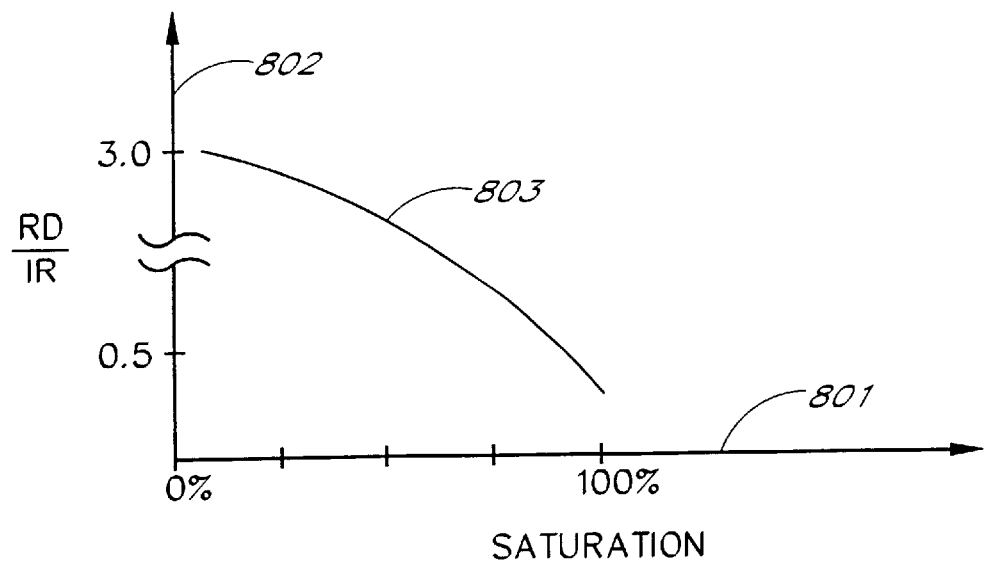
FIG. 8 is a graph which illustrates the relationship between the red/infrared ratio and blood oxygen saturation.
Figure 9:
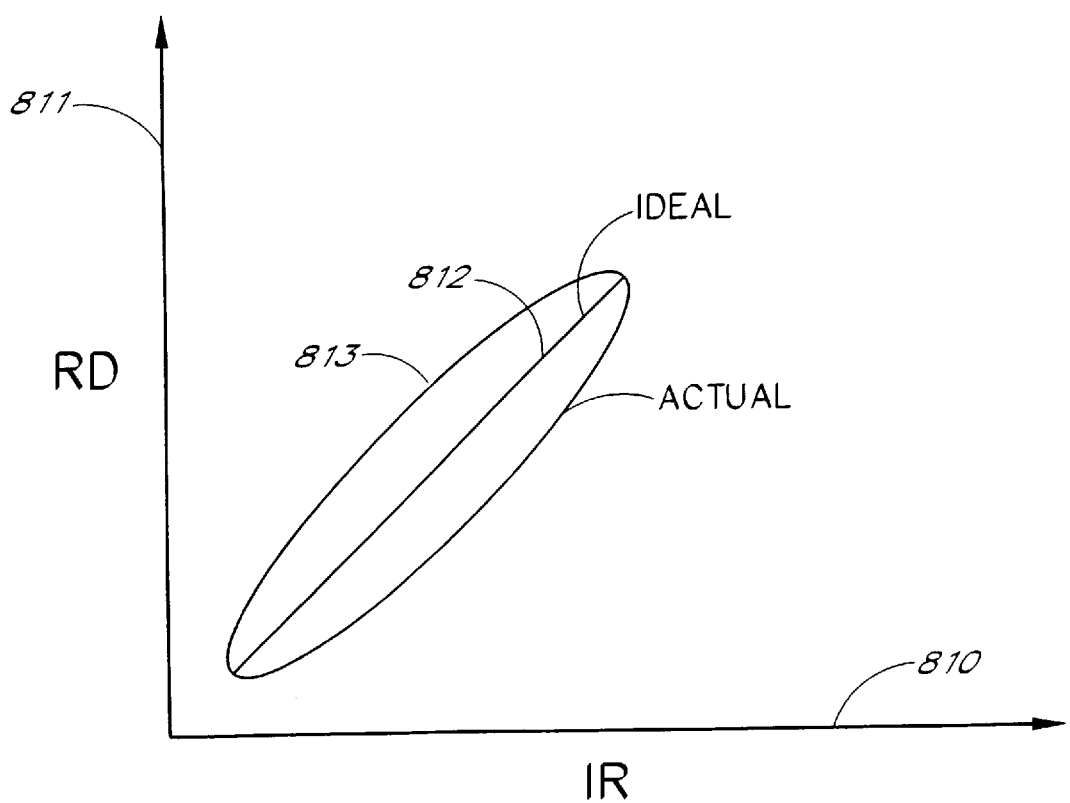
FIG. 9 is a graph which illustrates the relationship between the ideal red and infrared signals, and the relationship between measured red and infrared signals.

FIG. 9 shows a plot of RD(t) versus IR(t). In FIG. 9, an x axis 810 corresponds to IR(t) and a y axis 811 corresponds to RD(t). A straight line 812, having a positive slope, illustrates how the plot of RD(t) versus IR(t) would appear under ideal conditions of no noise, no scattering, and no motion artifacts. A curve 813 depicts a more realistic locus of points RD(t) versus IR(t) under normal measurement conditions. FIG. 8 shows a plot of blood oxygen saturation versus the ratio of the RMS value of RD(t)/IR(t). FIG. 8 shows an x axis 801 corresponding to blood oxygen saturation from 0% to 100% and a y axis corresponding to RMS(RD(t))/RMS(IR(t)) ranging from 0 to 3. A saturation curve 803 depicts the relationship between RMS(RD(t))/RMS(IR(t)) and blood oxygen saturation. The blood oxygen saturation is given by sat=$100*C_{HbO2}/(C_{Hb}+C_{HbO2})$. It is obtained by dividing Equation (10) by Equation (11) and solving for $C_{HbO2}$ and $C_{Hb}$ using the measured values of RD(t) and IR(t), and the known values of the absorption coefficients. Note that the unknown quantity d(t) is approximately the same for both red and infrared and thus divides out.

Detection and Removal of Motion Artifacts

Figure 10:
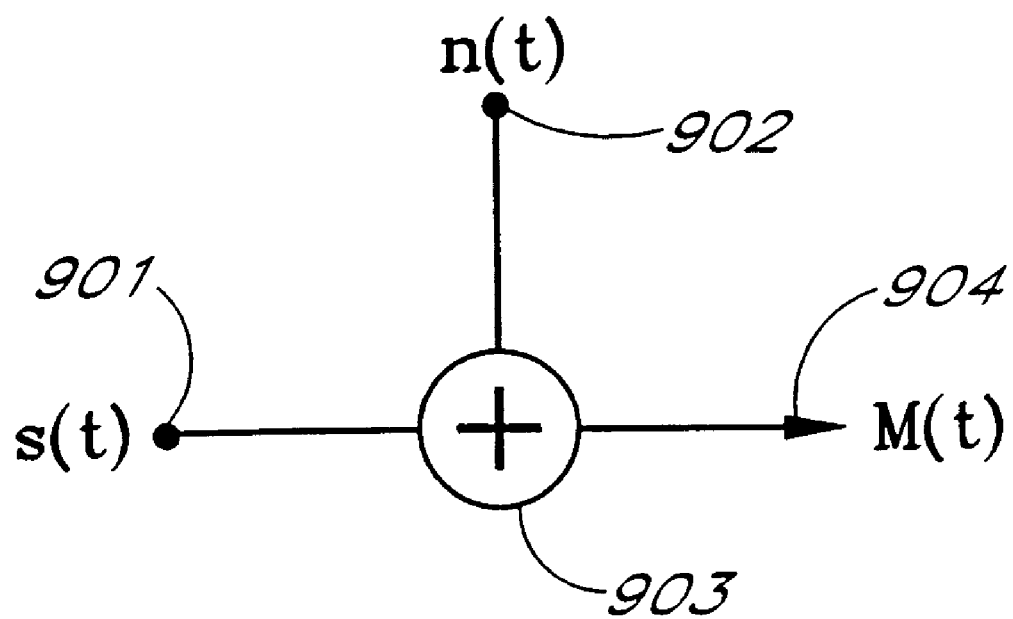
FIG. 10 illustrates a model for measured data in a pulse oximeter.

Persons skilled in the art know that the data obtained during pulse oximetry measurements using red and infrared light are often contaminated due to motion. Identification and removal of these motion artifacts is often a prerequisite to any signal processing used to obtain blood oxygen saturation, pulserate, or other physiological data. FIG. 10 schematically illustrates an additive noise process model that can be used, in conjunction with Equation (10) and Equation (11) to approximate the measured data contaminated by such motion artifacts. FIG. 9 shows a desired signal input s(t) 901 and an undesired signal input n(t) 902. The desired signal s(t) 901 and the undesired signal input n(t) 902 are summed by a summing junction 903. The output of the summing junction 903 represents the actual measured data M(t) 904. As applied to Equation (10), the desired signal s(t) 901 corresponds to RD(t). As applied to Equation (11), the desired signal s(t) 901 represents IR(t).

In FIG. 10, the desired signal s(t) 901, which contains the desired physiologic data is not directly accessible. Only the measured signal M(t) 904 is accessible. Thus, the problem is to obtain an estimate of the undesired signal n(t) 902 so that it can be subtracted from the measured signal to yield the desired signal. One such method for removing the undesired signal n(t) involves the use of a correlation canceler as is found in U.S. Pat. No. 5,432,036 (the '036 patent) assigned to the same assignee as the present application.

The correlation canceler is a complex operation requiring significant computational overhead. In accordance with one embodiment of the present invention, a new and novel method for detecting the presence of motion artifacts and removing these artifacts can be found in the spectral domain representations of the signals RD(t) and IR(t). Use of the spectral domain representations is more compatible with many of the digital signal processor (DSP) devices currently available. Further, the use of the spectral domain representations provides a method, as disclosed below, a way to estimate the amount of motion and noise separately. As a further advantage, it is noted that, under certain circumstances, the correlation canceler would drive the output signal to zero. The spectral domain method of detecting artifacts is far less likely to drive the output signal to zero.

Figure 11:
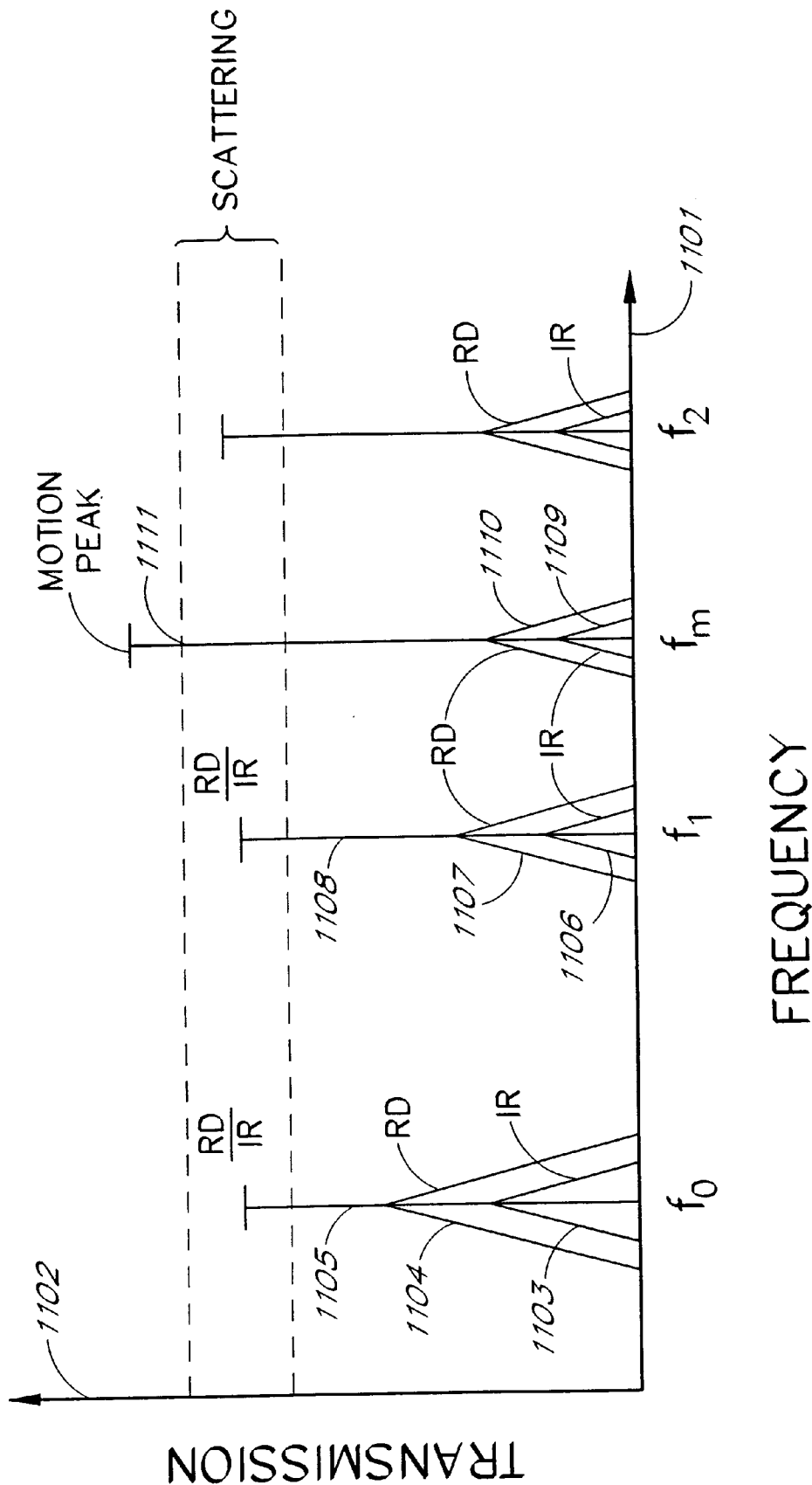
FIG. 11 is an idealized frequency domain plot of the red and infrared transmission signals

FIG. 11 shows an idealized illustration of the spectrum of RD(t) and IR(t). FIG. 11 shows an x axis 1101 corresponding to frequency, and a y axis 1102 corresponding to the magnitude of the spectral components. The spectrum of RD(t), denoted mathematically as:

$$RD(\omega) = \mathscr{F}\,[RD(t)] \qquad (12)$$

is shown as a series of peaks, comprising a first spectral peak 1104 at a fundamental frequency $f_0$, a second spectral peak 1107 at a first harmonic $f_1$ and a third spectral peak 1110 at a frequency $f_m$. The spectrum of IR(t), denoted mathematically as:

$$IR(\omega) = \mathscr{F}\,[IR(t)] \qquad (13)$$

is shown as a series of peaks, comprising a first spectral peak 1103 at the fundamental frequency $f_0$, a second spectral peak 1106 at the first harmonic $f_1$ and a third spectral peak 1109 at a frequency $f_m$. The ratio of the spectral components, given by $RD(\omega)/IR(\omega)$, is shown as a first ratio line 1105 at the fundamental frequency $f_0$, a second ratio line 1108 at the first harmonic $f_1$ and a third ratio line 1111 at the frequency $f_m$. As discussed below, when there are no motion artifacts in the spectrum of FIG. 11, all of the spectral peaks will occur at harmonic frequencies, and all of the ratio lines will have approximately the same height. Under conditions of no motion, difference in the height of the ratio lines will be due primarily to scattering effects. The spectral peaks 1110 and 1109 corresponding to the frequency $f_m$, which is not necessarily a harmonic of $f_0$, represent peaks due to motion, and therefor having an amplitude different from that of the first spectral line 1105 and the second spectral line 1108.

One skilled in the art will recognize that the representations in FIG. 11 have been idealized for the purposes of explanation. In particular, in actual measured data, especially data contaminated by noise and other undesired components, the frequencies of the spectral peaks of $RD(\omega)$ do not correspond exactly to the spectral peaks of $IR(\omega)$. Although corresponding frequencies will typically be quite close, variations of a few percent are not unexpected. Thus, for example, it will be obvious to one skilled in the art that, due to the imperfections in most measured data, the fundamental frequency $f_0$ found for $RD(\omega)$ will often be different from the fundamental frequency $f_0$ found for $IR(\omega)$. The same comments would apply to other harmonics (e.g., $f_1$ and $f_2$) as well. In one embodiment of the present invention, the frequencies $f_0$, $f_1$, $f_2$ (or equivalently $\omega_0$, $\omega_1$, $\omega_2$), etc. (hereinafter the frequency peaks) correspond to the frequency peaks found in $RD(\omega)$, and the ratios $RD(\omega)/IR(\omega)$ are calculated using the values of $RD(\omega)$ and $IR(\omega)$ at those frequencies, regardless of whether they also happen to correspond to a frequency peak in $IR(\omega)$. In another embodiment of the present invention, the frequency peaks correspond the frequency peaks found in $IR(\omega)$, and the ratios $RD(\omega)/IR(\omega)$ are calculated using the values of $RD(\omega)$ and $IR(\omega)$ at those frequencies, regardless of whether they also happen to correspond to a frequency peak in $RD(\omega)$. In yet another embodiment of the present invention, the frequency peaks of $RD(\omega)$ and $IR(\omega)$ are found separately, and the ratios $RD(\omega)/IR(\omega)$ are calculated by matching the frequency peaks of $RD(\omega)$ with the nearest frequency peaks of $IR(\omega)$.

In an ideal measurement, the red and infrared spectra are the same to within a constant scale factor. Thus, in an ideal measurement, all of the ratio lines 1105, 1108 and 1111 have substantially the same amplitude. Any differences in the amplitude of these lines is likely due to motion or other contaminations represented by n(t) (including scattering effects). For each component, red and infrared, the model of FIG. 9 can be expressed as:

$$S_1(t) = A(t) + N(t) \qquad (14)$$
$$S_2(t) = rA(t)h(t) + \mu N(t)\eta(t)$$
$$\approx rA(t) + \mu N(t)$$

where $S_1(t)$ represents the infrared signal, A(t) represents the desired infrared signal and N(t) represents the noise signal. Likewise, $S_2(t)$ represents the measured red signal, r represents the ratio of red to infrared ($RD(\omega)/IR(\omega)$) expected in an uncontaminated measurement, and $\mu$ represents the ratio of red noise to infrared noise. The quantities h(t) and $\eta(t)$ are primarily due to scattering, and thus required because, strictly speaking, A(t) and N(t) in the red channel and infrared channels are not simply related by a constant. However, for most purposes, the quantities h(t) and $\eta(t)$ are sufficiently close to unity that they can be ignored.

Introducing an arbitrary scaling factor $\alpha$ into the equation for $S_1$, and then subtracting the two equations yield (for notational convenience, the time dependence of S, A and N will not be explicitly shown):

$$\alpha S_1 - S_2 = A(\alpha - r) + N(\alpha - \mu) \qquad (15)$$

Two special cases arise from Equation (15). First, when $\alpha = r$, Equation (15) reduces to:

$$N = \frac{\alpha S_1 - S_2}{r - \mu} \qquad (16)$$

Second, when $\alpha = \mu$, Equation (17) reduces to:

$$A = \frac{\alpha S_1 - S_2}{\mu - r} \qquad (17)$$

The values of $\mu$ and r can be found from the ratio of $RD(\omega)/IR(\omega)$ as shown in FIG. 11 and the following two observations. First, since r is the coupling coefficient between red and infrared (the ratio of red to infrared) then r is expected to be reasonably constant over short periods of time. Likewise, $\mu$ is expected to be relatively constant because it is merely the coupling coefficient between the noise in the red and infrared signals. Second, the condition $\mu = r$ is not expected to occur because that would mean that the saturation due to arterial blood is equal in magnitude to the saturation due to venous blood. One skilled in the art will recognize, that, except for short periods of time, arterial blood saturation and venous blood saturation cannot be the same, because a living body consumes oxygen from the blood as the blood passes from the arteries to the veins. Arterial blood and venous blood saturation can be the same for short periods of time, and even reversed, especially where blood pooling has occurred and a quick desaturation is taking place. It is always expected that $\mu$ is larger than r. Therefore, in one embodiment of the present invention, the value of $\mu$ corresponds to the largest peak in FIG. 11 and the value of r corresponds to the smallest peak of FIG. 11. Further, the presence of motion artifacts in the data are easily detectable by examination of the relationship between $\mu$ and r.

In a preferred embodiment, the value of $\mu$ is found by classifying the ratio peaks according to a ratio threshold g. The ratio threshold g is computed identifying the first N ratio lines $R_N$ associated with the first N spectral peaks. The ratio threshold g is then computed as a modified center of mass for the $R_N$ lines according to the following equation.

$$g = \frac{N}{\sum_{i=0}^{N-1} \frac{1}{R_i}}$$

Each ratio line is then compared with the ratio threshold g. Only those ratio lines whose magnitude is larger than the ratio threshold g are included in a set Y of ratio lines. Only ratio lines in the set Y are used in the calculation of $\mu$. In one embodiment, the value of $\mu$ is the magnitude of the largest ratio peak in the set of ratio peaks $R_i$ for i=0 . . . N. In an alternate embodiment, the value of $\mu$ is the magnitude of the ratio peak corresponding to the largest spectral peak in the set Y.

The values of $\mu$ and r are used to determine whether motion artifacts are present. In one embodiment, the ratio $\mu/r$ is calculated. If the ratio is close to unity, then, to within a constant scaling factor, the spectrum RD($\omega$) is approximately the same as the spectrum IR($\omega$) and thus there are no motion artifacts. If, on the other hand, the ratio $\mu/r$ is not close to unity, then the shape of the spectrum RD($\omega$) is different from the spectrum IR($\omega$), signaling the presence of motion artifacts, and thus the spectrum must be scrubbed according to Equation (17).

In a preferred embodiment, a delta is computed by subtracting the magnitude of the smallest ratio line from the magnitude of the largest ratio line. If the delta is smaller than a threshold value, then the spectrum RD($\omega$) is approximately the same as the spectrum IR($\omega$) and thus there are no motion artifacts, but only variations due to scattering. If, on the other hand, the delta $\mu-r$ is greater than the threshold value, then the shape of the spectrum RD($\omega$) is different from the spectrum IR($\omega$), signaling the presence of motion artifacts, and thus the spectrum must be scrubbed according to Equation (15).

Figure 12:
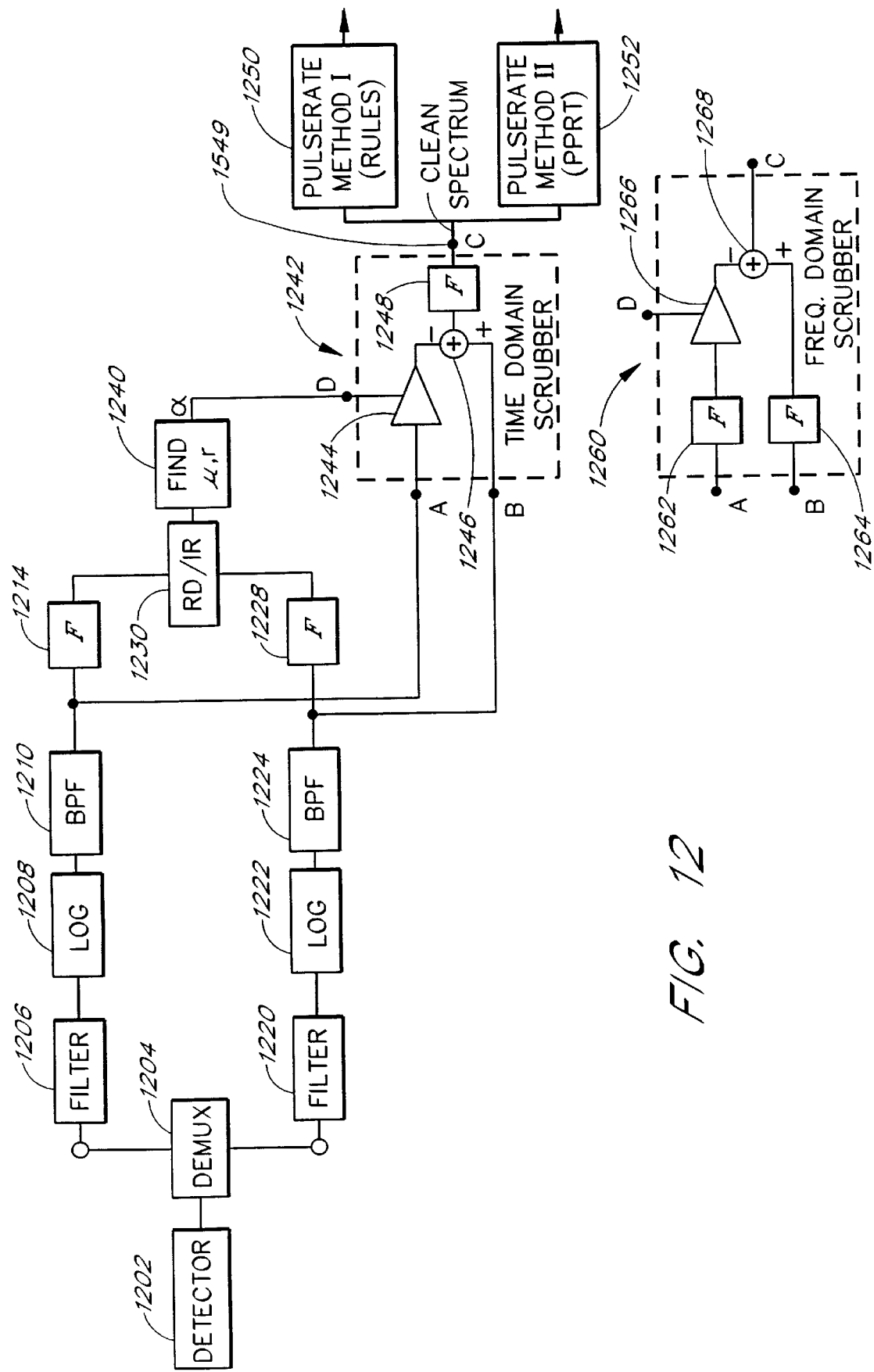
FIG. 12 is a block diagram of a motion detector and removal system in accordance with one aspect of the present invention.

FIG. 12 shows a block diagram of a signal processing system that implements the motion detection and spectrum scrubbing operations in accordance with one aspect of the present invention. In FIG. 12, an input from a single sensor 1202 that receives red and infrared light is fed into a demultiplexer 1204 which separates the red and infrared signals. The red signal is fed into a filter 1206 which removes unwanted spectral components. The output of the filter 1206 is normalized (as is described in the text describing FIG. 7) by the series combination of a log amplifier 1208, and a bandpass filter 1210. The output RD(t) of the bandpass filter 1210 is fed into a Fourier transform block 1214. The output of the transform block 1214 is fed into the numerator term of a divider 1230. The infrared output from the demultiplexer 1204 is processed, in the same fashion as the red signal, by the series combination of a filter 1220, a log amplifier 1222, a bandpass filter 1224, and a Fourier transform block 1228. The output of the Fourier transform block 1228 is fed into a denominator input of the divider 1230. An output of the divider 1230 is fed into a process block 1240 which determines $\mu$, and r, and which computes $\alpha$ according to the flowchart of FIG. 13. An a output of the process block 1240 is fed as an input to a time domain waveform scrubber 1242. The time domain waveform scrubber 1242 has three input terminals, A, B, and D, and a single output terminal C. The time domain scrubber terminal A is connected to the output of the bandpass filter 1210. The time domain scrubber terminal B is connected to the output of the bandpass filter 1224. The time domain scrubber terminal D is connected to the $\alpha$ output of the process block 1240. Inside the time domain scrubber 1242, the terminal A is connected to a signal input of a gain controlled amplifier 1244. A gain control input of the amplifier 1244 is connected to the scrubber terminal D. The scrubber terminal B is connected to a plus input of an adder 1246. An output of the amplifier 1244 is connected to a minus input of the adder 1246. An output of the adder 1246 is connected to a Fourier transform block 1248. An output of the Fourier transform block 1248 is connected to the scrubber output terminal C.

One skilled in the art will recognize that the linearity of the Fourier transform allows the scrubbing operation to be carried out in the frequency domain as well. A frequency domain scrubber 1240 is also shown in FIG. 12. The frequency domain scrubber 1260 has the same four terminals, A, B, C, and D, as the time domain scrubber 1242.

Inside the frequency domain scrubber 1260, the terminal A is connected to a signal input of a Fourier transform block 1262. The output of the Fourier transform block 1262 is connected to a signal input of a gain controlled amplifier 1266. A gain control input of the amplifier 1266 is connected to the scrubber terminal D. The scrubber terminal B is connected to a Fourier transform block 1264. An output of the transform block 1264 is connected to a plus input of an adder 1268. An output of the amplifier 1266 is connected to a minus input of the adder 1268. An output of the adder 1268 is connected to the scrubber output terminal C.

Regardless of whether the time domain scrubber 1242 or the frequency domain scrubber 1260 is used, the scrubber output C is a plethysmographic waveform in the frequency domain at a terminal 1249. Ideally, the waveform at terminal 1249 is cleaner (e.g., has a better signal to noise ratio) than the waveform at either scrubber input A or scrubber input B. The waveform at terminal 1249 can be displayed on a display (not shown) or sent to a rule based pulserate detector 1250 and/or a transform based pulserate detector 1252.

Figure 13:
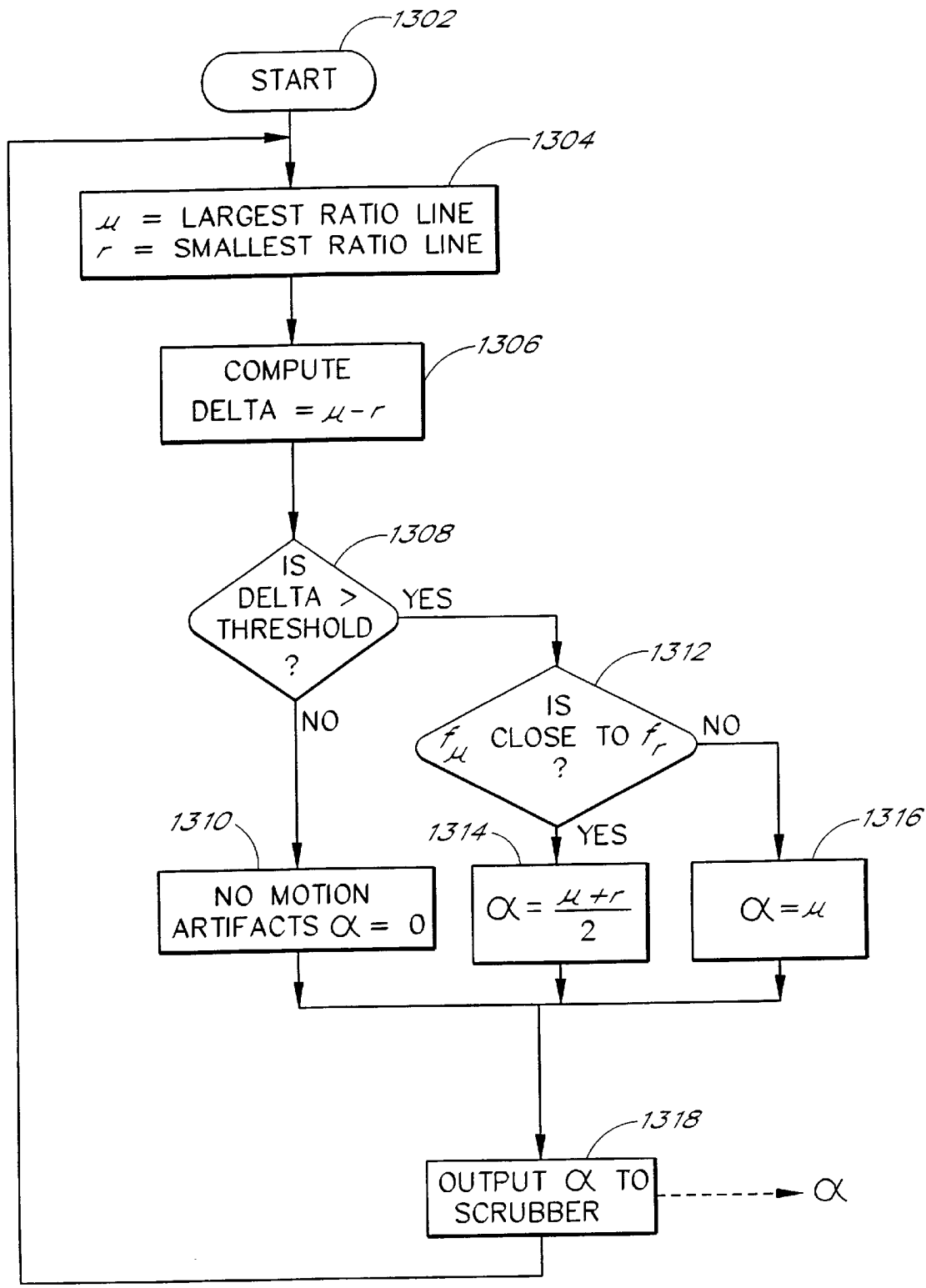
FIG. 13 is a flowchart showing the processing steps of a motion detector and removal method in accordance with one aspect of the present invention.

FIG. 13 is a flowchart which illustrates the process steps performed by the signal processing block 1240 in FIG. 12. The flowchart of FIG. 13 begins at a start block 1302 and proceeds to a process block 1304. In the process block 1304, the spectrum F($\omega$)=RD($\omega$)/IR($\omega$) is searched for the largest ratio line $\mu$ and smallest ratio line r and the frequencies $f_\mu$ and $f_r$ at which those two lines occur. The process then advances to a process block 1306 where the difference, delta d=$\mu-r$ is computed. The process then proceeds to a decision block 1308. If, in the decision block 1308, the delta d is greater than a threshold value, then motion artifacts are present and the process advances to a decision block 1312 to continue the calculation of $\alpha$. Otherwise, if in the process block 1308, the delta d is less than the threshold value, then no scrubbing is necessary and the process advances to a process block 1310. Since both $\mu$ and r are ratios, they are dimensionless. The delta d is also dimensionless. In a preferred embodiment, the threshold value is 0.5. In the process block 1310, the value of $\alpha$ is set to 0, which essentially disables the scrubber. In the decision block 1312, the frequencies $f_\mu$ and $f_r$ are compared. If the two frequencies are close together, then the process advances to a process block 1314; otherwise, the process advances to a process block 1316. In the process block 1314 the value of $\alpha$ is set to $\alpha=(\mu+r)/2$. In the process block 1316 the value of $\alpha$ is set to a=$\mu$. The process blocks 1310, 1314 and 1316 all advance to a process block 1318 where the value of $\alpha$ is sent to the scrubber. Upon completion of the process block 1318, the process jumps back to the process block 1304 to recalculate α.

One skilled in the art will recognize that the flowchart in FIG. 13 can be modified to perform additional functions. For example, upon detecting that motion artifacts are present (during the transition to the decision block 1312), an indicator can be lit, or an alarm can be sent, to warn the medical clinician that motion artifacts were present. In yet another embodiment, upon transitioning to the process block 1312, the delta d could be examined against a second threshold to determine whether the motion artifacts were so severe that further processing was impossible.

Rule Based Pulserate Detection

In addition to measuring blood oxygen saturation, a pulse oximeter is able to perform continuous monitoring of a patient's pulserate. As shown in FIG. 6, each heartbeat forces blood into the arteries and that increase in blood is detected by the plethysmographic apparatus. Thus, the scrubbed spectrum present at the terminal 1250 in FIG. 12 contains some of the information that would be found in the Fourier spectrum of an electrocardiograph (EKG).

Figure 14A:
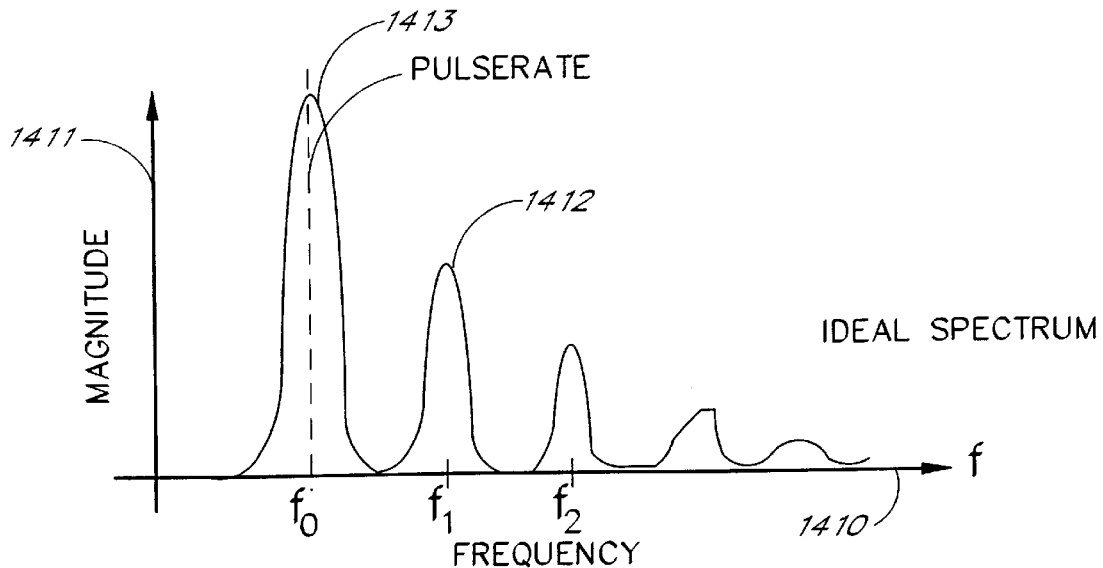
FIG. 14A is an idealized frequency domain plot of an plethysmographic wave.

FIG. 14A shows an ideal spectrum $F(\omega)$ of a clean plethysmographic wave from a heart that is beating with a very regular beat. The figure shows an x axis 1410 corresponding to frequency and a y axis 1411 corresponding to the magnitude of the spectral components. A curve 1412 shows $|F(\omega)|$. It is well known, that the waveform of a human heartbeat is not a pure sine wave, and thus the curve 1412 is not a single spectral line, but rather a first spectral line at a fundamental frequency $f_0$ and a series of decreasing harmonics at $2f_0$, $3f_0$, etc. Clearly, under these conditions, the frequency $f_0$ corresponds to the pulserate.

Figure 14B:
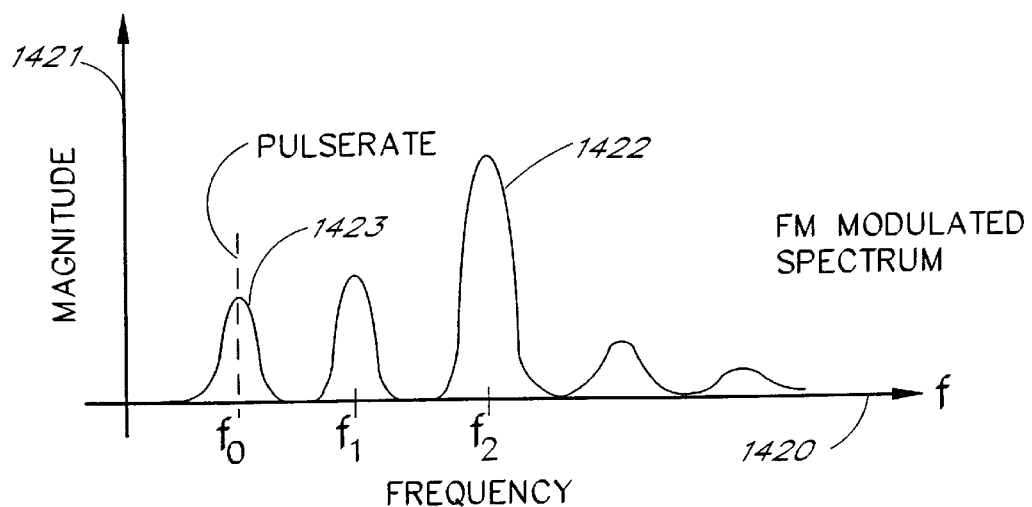
FIG. 14B is an idealized frequency domain plot of a plethysmographic wave showing the effect of FM modulation.

Often the ideal waveform of FIG. 14A is not seen because the heart is beating irregularly or because the cardiovascular system of the subject is producing a large dicrotic notch. This leads to a spectrum in which the largest spectral line is not necessarily the pulserate. FIG. 14B shows one example of such a waveform. Like FIG. 14A, FIG. 14B shows an x axis 1420 corresponding to frequency, and a y axis 1421 corresponding to amplitude. A curve 1422 shows $|F(\omega)|$. However, unlike the curve 1412, the curve 1422 shows a spectral line at a fundamental frequency $f_0$, and a series of harmonics $f_1$ and $f_2$ having amplitudes larger than the amplitude of the fundamental, with $f_2$ being the largest. The curve 1422 illustrates the folly of attempting to determining pulserate merely by finding the largest spectral line. Such an algorithm, applied to the curve 1422 would report a pulserate that was three times higher than the actual pulse rate.

Figure 14C:
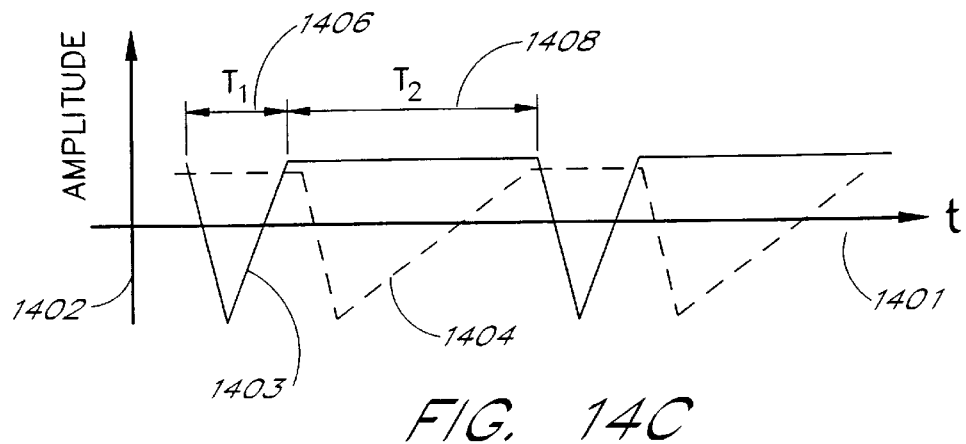
FIG. 14C is an idealized time domain plot of a superimposed pair of plethysmographic waves that can be used to model an FM modulated plethysmographic wave.

The spectrum shown in curve 1422 is commonly seen in plethysmographic waveforms and corresponds to a frequency modulated (FM heartbeat. In accordance with one aspect of the present invention, a rule based method for determining the pulserate of a heart producing the spectrum of FIG. 14B is disclosed. The rule based method is based on a time domain model (a "stick model") plotted in FIG. 14C. This elegantly simple model captures the essential feature of the plethysmographic waveform. FIG. 14C shows an x axis 1401 corresponding to time, and a y axis 1402 corresponding to the amount of blood being forced into the arteries by a heart. FIG. 14C further shows two overlapping waveforms. A first waveform 1403 shows to blood being forced into the arteries during a first time interval $T_1$. A second waveform 1404 shows blood being forced into the arteries during a second time interval $T_2$. The two time intervals, $T_1$ and $T_2$, do not overlap and the total period of the sum of the two waveforms is $T_1+T_2$. The sum of the two waveforms represents a heart that is beating at two different pulserates on alternate beats. For example, if the heartbeats were numbered, then on every even numbered beat, the heartbeat would last $T_1$ seconds. On every odd numbered beat, the heartbeat would last $T_2$ seconds. This is not an unusual occurrence, and there are physiological reasons why this occurs. The spectrum shown in FIG. 14B is essentially the spectrum of the superposition of the waveforms 1403 and 1404.

Figure 15:
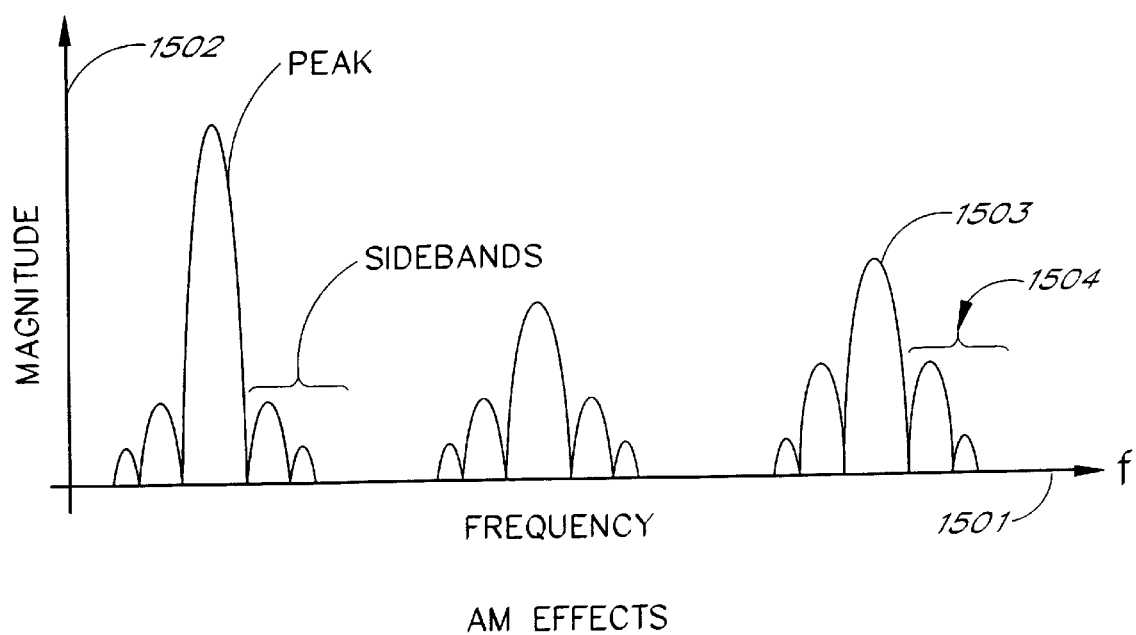
FIG. 15 is an idealized frequency domain plot of a plethysmographic wave showing the effects of AM modulation.

Amplitude modulation (AM) of the plethysmographic waveform is also possible and common. Amplitude modulation occurs primarily when the heart beats with different strength on different heartbeats. FIG. 15 shows a sample spectrum $F(\omega)$ that exhibits the effects of AM. FIG. 15 shows a frequency axis 1501 and a spectrum axis 1502. The spectrum consists of a series of spectral peaks 1503 and sidebands 1504. One skilled in the art will recognize this as a typical AM spectrum of a carrier and its associated modulation sidebands. Under some conditions, of high pulserate and substantial modulation bandwidth, the sidebands 1504 due to one spectral peak 1503 can overlap the sidebands due to an adjacent spectral peak. This overlap significantly complicates the waveform (not shown).

Figure 16A:
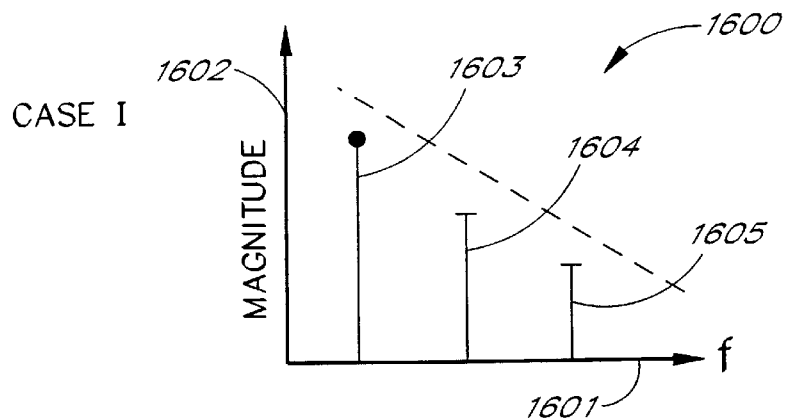
FIG. 16 is a group of idealized frequency domain plots that illustrate the various categories used in the rule based method for determining pulserate in accordance with one aspect of the present invention.
Figure 16B:
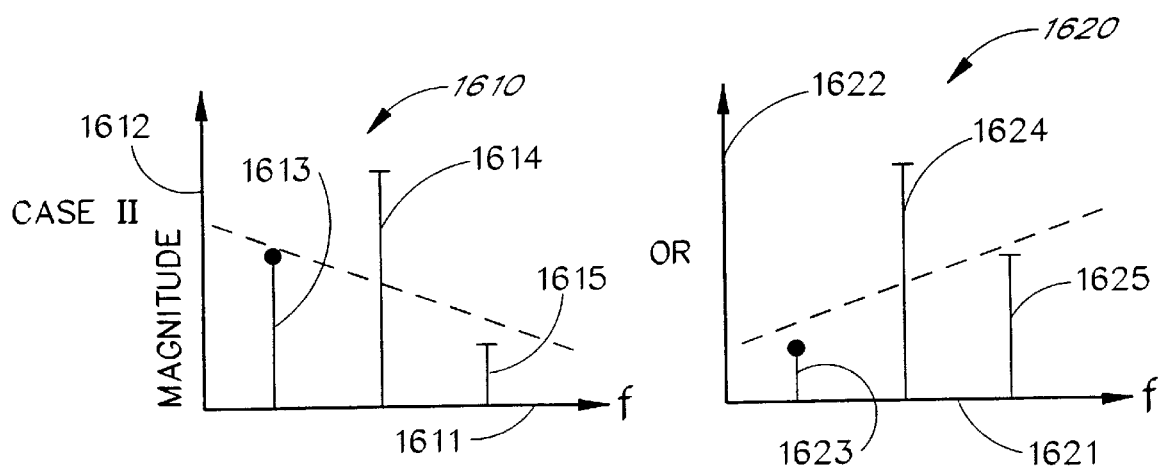
Figure 16C:
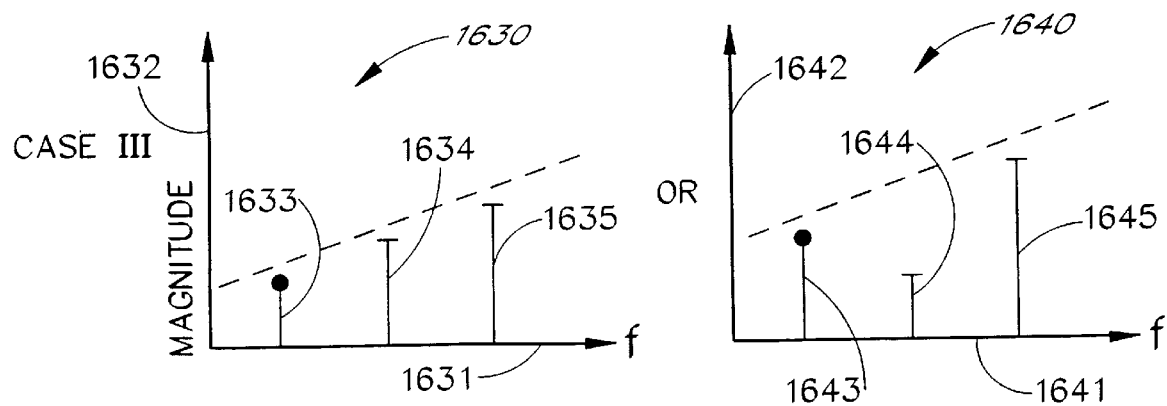

In accordance with one aspect of the present invention, the pulserate can be determined in the presence of FM and AM distortions by classifying the spectrum as one of five categories grouped into three cases. The five categories are illustrated as idealized graphs in: FIG. 16A, illustrating Case I; FIG. 16B, illustrating Case II; and FIG. 16C, illustrating Case III.

FIG. 16A shows a plot 1600 having an x axis 1601 corresponding to frequency and a y axis 1602 corresponding to the magnitude of the spectrum. FIG. 16A also shows a first spectral line 1603, a second spectral line 1604 and a third spectral line 1605. The three spectral lines 1603, 1604, and 1605 show a monotonically decreasing amplitude where the decrease is approximately linear.

FIG. 16B shows a first plot 1610 having an x axis 1611 corresponding to frequency and a y axis 1612 corresponding to the magnitude of the spectrum. The first plot 1610 also shows a first spectral line 1613, a second spectral line 1614 and a third spectral line 1615. The third spectral line 1615 has the smallest amplitude of the three lines. The second spectral line 1614 has the largest amplitude of the three lines, and its amplitude rises significantly above a line drawn from the first spectral line 1613 to the third spectral line 1615.

FIG. 16B also shows a second plot 1620 having an x axis 1621 corresponding to frequency and a y axis 1622 corresponding to the magnitude of the spectrum. The second plot 1620 also shows a first spectral line 1623, a second spectral line 1624 and a third spectral line 1625. The first spectral line 1623 has the smallest amplitude of the three lines. The second spectral line 1624 has the largest amplitude of the three lines, and its amplitude rises significantly above a line drawn from the first spectral line 1623 to the third spectral line 1625.

FIG. 16C shows a first plot 1630 having an x axis 1631 corresponding to frequency and a y axis 1632 corresponding to the magnitude of the spectrum. The first plot 1630 also shows a first spectral line 1633, a second spectral line 1634 and a third spectral line 1635. The amplitudes of the three spectral lines are monotonically increasing, and the increase is approximately linear.

FIG. 16C also shows a second plot 1640 having an x axis 1641 corresponding to frequency and a y axis 1642 corresponding to the magnitude of the spectrum. The second plot 1640 also shows a first spectral line 1643, a second spectral line 1644 and a third spectral line 1645. The third spectral line 1645 has the smallest amplitude of the three lines. The second spectral line 1644 has the largest amplitude of the three lines, and its amplitude is significantly below a line drawn from the first spectral line 1643 to the second spectral line 1645.

In accordance with one aspect of the present invention, the pulserate is determined by identifying the largest three spectral lines, then matching the spectrum to one of the idealized spectra shown by the plots 1600, 1610, 1620, 1630, or 1640, and then applying one of a set of rules to determine the pulserate. It will be understood by one skilled in the art that, although the frequencies of the spectral shown in the plots 1600, 1610, 1620, 1630, or 1640 appear to be harmonically related. In practice the spectral lines may not correspond to frequencies which are harmonics.

Figures 18, 18A:
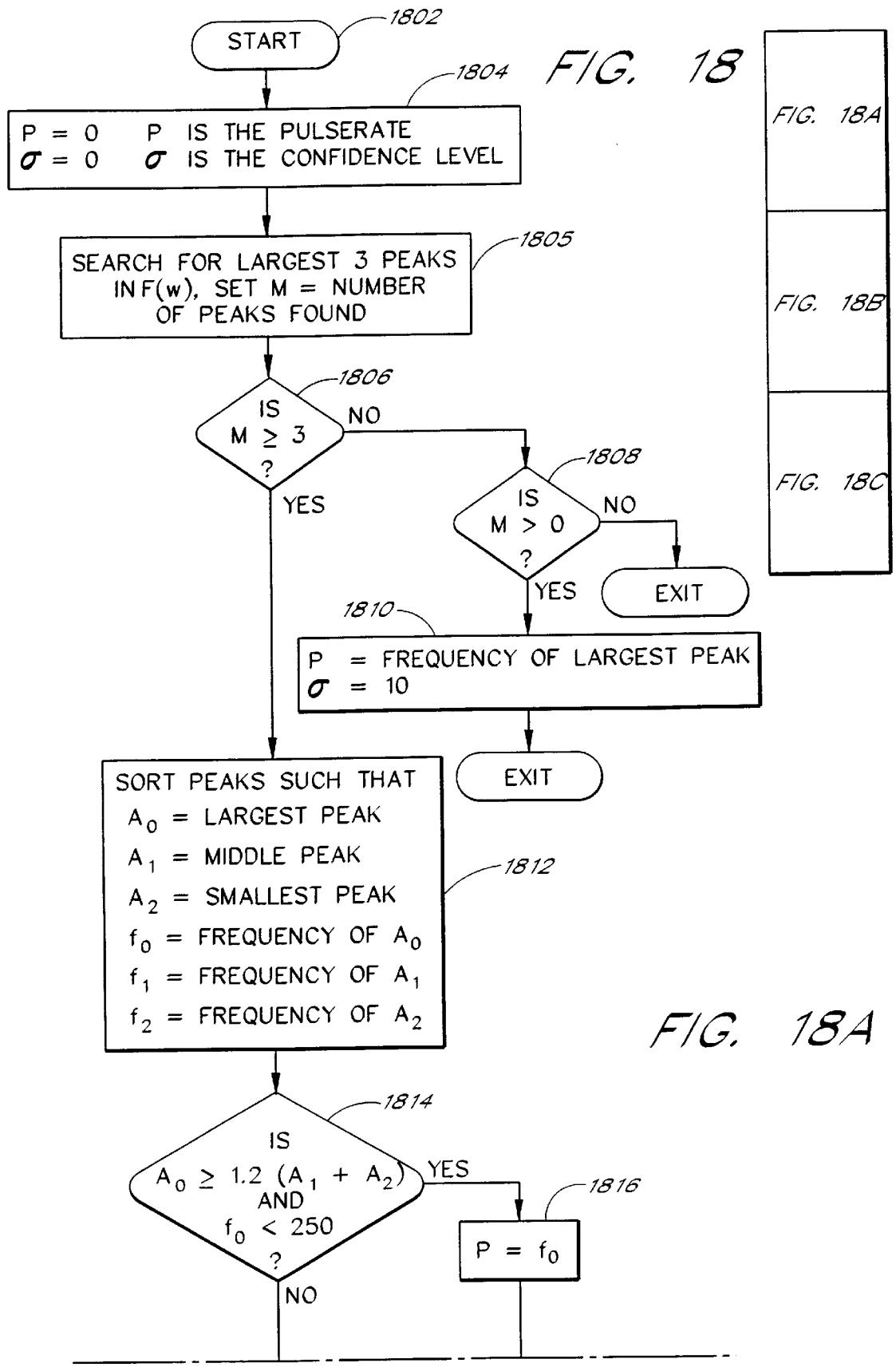
FIG. 18 is a flowchart showing the process steps of the rule based pulserate detection method.
Figure 18B:
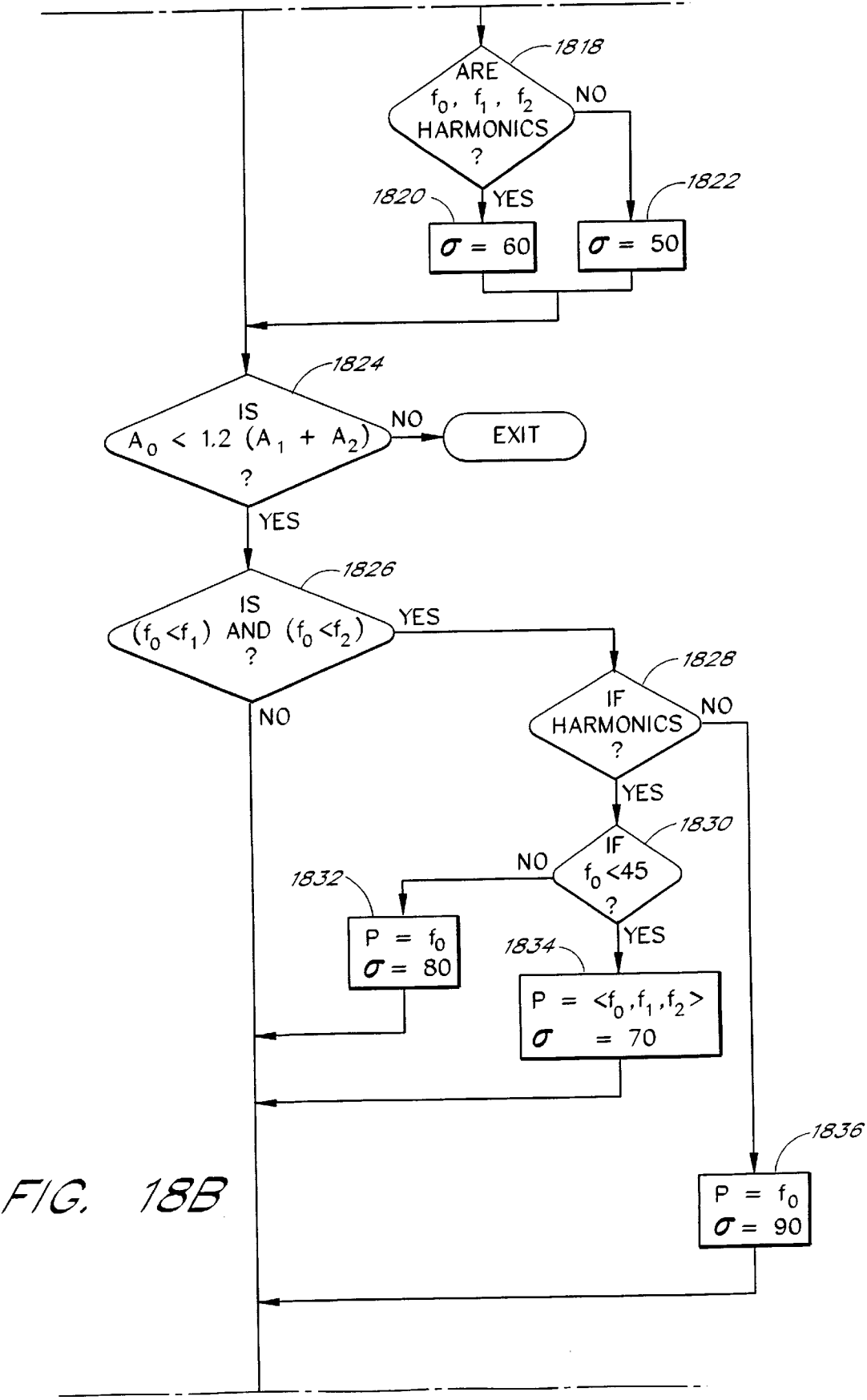
Figure 18C:
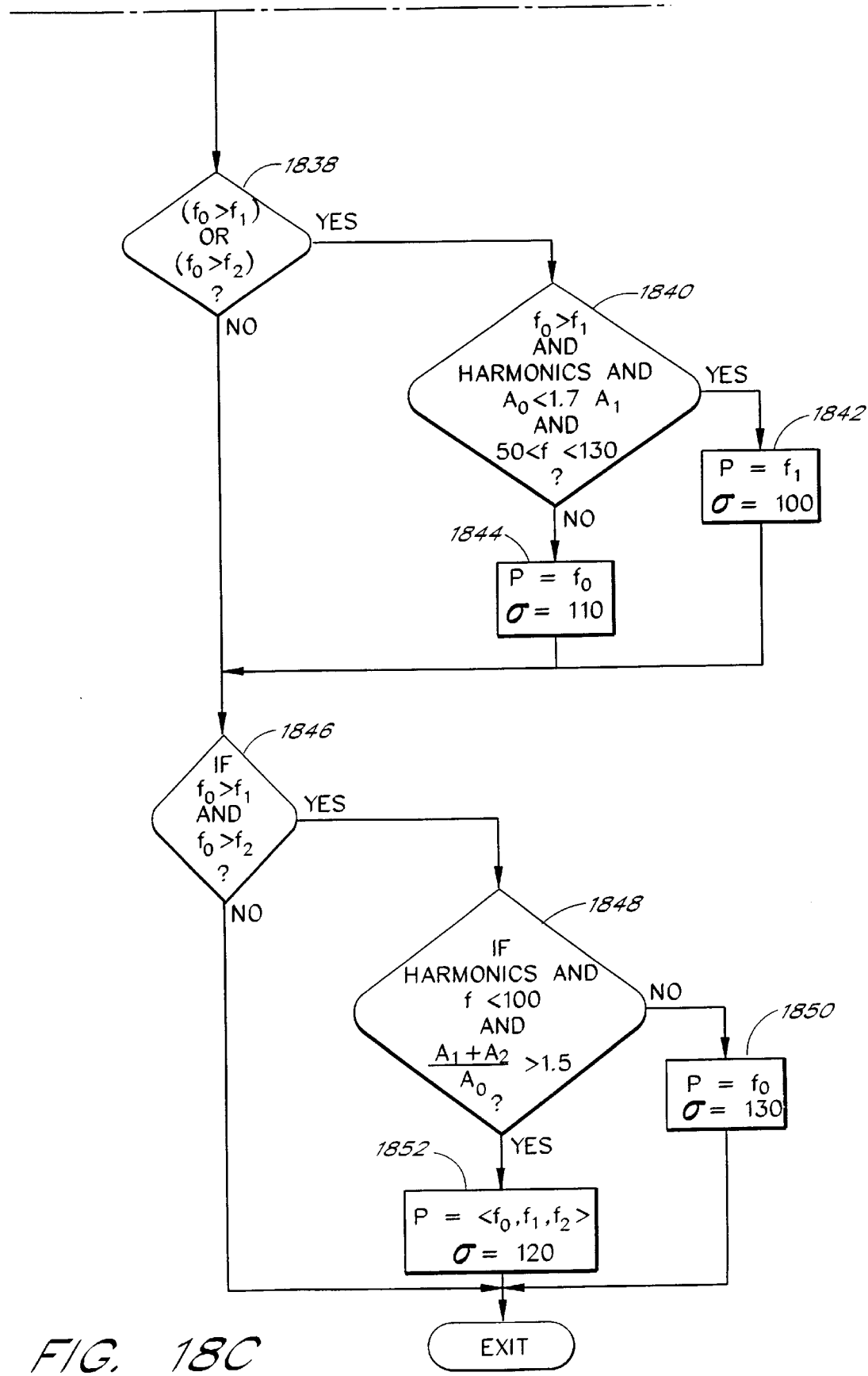

The details of the rule based process are shown in the flowchart of FIG. 18. FIG. 18 begins at a start block 1802 and proceeds to an initialization process block 1804. In the block 1804, the values of the pulserate, p, and confidence factor, s, are set to zero. When the process reaches an exit block, p will contain the pulserate (or zero if no pulserate was found), and σ will contain a confidence factor indicating related to the pulserate (or zero if no pulserate was found). After completing the initialization block 1804, the process advances to a search process block 1805 where the spectrum $|F(\omega)|$ is searched for the first three spectral peaks. After finding the peaks, the process advances to a decision block 1806 where the process checks the number of spectral peaks actually found. If, in the decision block 1806, the number of peaks is less than three, then the process advances to a decision block 1808; otherwise, the process jumps forward to a process block 1812. If, in the process block 1808, the number of peaks is greater than zero, then the process advances to a process block 1810; otherwise, the process jumps to an exit block. In the process block 1810, the value of p is set to the frequency corresponding to the largest of the spectral peaks, the confidence value is set to 10, and the process then advances to the exit block.

In the process block 1812, the first three spectral peaks are sorted by magnitude, and the values assigned to variables $A_0$, $A_1$, and $A_2$ such that $A_0$ is the magnitude of the largest peak, $A_1$ is the magnitude of the middle peak, and $A_2$ is the magnitude of the smallest peak. Also, in the process block 1812, variables $f_0$, $f_1$, and $f_2$, representing the frequencies corresponding to $A_0$, $A_1$ and $A_2$ respectively, are set. Upon completion of the process block 1812, the process advances to a decision block 1814. In the decision block 1814, if $A_0$ is greater than or equal to $1.2*(A_1+A_2)$ and $f_0$ is less than 250, then the process advances to a process block 1816; otherwise the process jumps to a decision block 1824. In the process block 1816, the value of p is set to $p=f_0$, and the process then advances to a decision block 1818. In the decision block 1818, the values of $f_0$, $f_1$, and $f_2$ are checked to see if they are harmonics of one another. In a preferred embodiment, this is done by checking to see whether a frequency $f_i$ is within ten beats per minute of being a integer multiple of another frequency $f_j$ (where ij=0, 1, or 2). If the decision block 1818 detects that the frequencies are harmonics, then the process advances to a process block 1820; otherwise, the process advances to a process block 1822. In the process block 1820, the value of σ is set to 60, and the process then advances to the decision block 1824. In the process block 1822, the value of σ is set to 50 and the process then advances to the decision block 1824.

In the decision block 1824, if $A_0<1.2*(A_1+A_2)$, then the process advances to a decision block 1826, otherwise the process advances to the exit block. In the decision block 1826, if $(f_0<f_1)$ and $(f_0<f_2)$, then the process advances to a decision block 1828; otherwise the process advances to a decision block 1938. In the decision block 1828, if the frequencies $f_0$, $f_1$, and $f_2$ are harmonics, then the process advances to a decision block; otherwise, the process advances to a process block 1836. In the process block 1836, the value of p is set to $p=f_0$, the value of σ is set to 90, and the process then advances to the decision block 1838. In the decision block 1830, if $f_0$ is less than 45 beats per minute, then the process advances to a process block 1834; otherwise, the process advances to a process block 1832. In the process block 1832, the value of p is set to $p=f_0$, the value of σ is set to σ=80, and the process then advances to the decision block 1838. In the process block 1834, the value of p is set to $p=(f_0+f_1+f_2)/3$, the value of σ is set to σ=70, and the process then advances to the decision block 1838.

In the decision block 1838, if $f_0>f_1$ or $f_0>f_2$, then the process advances to a decision block 1840; otherwise, the process advances to a decision block 1846. In the decision block 1840, if $(f_0>f_1)$ and $(f_0, f_1$ and $f_2$ are harmonics) and $(A_0<1.7A_1)$ and $(30<f_1<130)$ then the process advances to a decision block 1842; otherwise, the process advances to a process block 1844. In the process block 1842, the value of p is set to $p=f_1$, the value of σ is set to σ=100, and the process then advances to the decision block 1848. In the process block 1844, the value of p is set to $p=f_0$, the value of σ is set to σ=110, and the process then advances to the decision block 1848.

In the decision block 1848, if ($f_0$, $f_1$ and $f_2$ are harmonics) and $f_0<100$ and $((A_1+A_2)/A_0>1.5)$, then the process advances to a process block 1852; otherwise, the process advances to a process block 1850. In the process block 1852, the value of p is set to $p=(f_0+f_1+f_2)/3$, the value of σ is set to σ=120, and the process then advances to the exit block. In the process block 1852, the value of p is set to $p=f_0$, the value of σ is set to σ=130, and the process then advances to the exit block.

As stated previously, when the process shown in FIG. 18 reaches the exit block, p contains the pulserate, and σ contains the confidence factor. The confidence factor is a number indicating the likelihood that the value of p accurately represents the actual pulserate of the patient.

Transform Based Pulserate Detection

Figure 17:
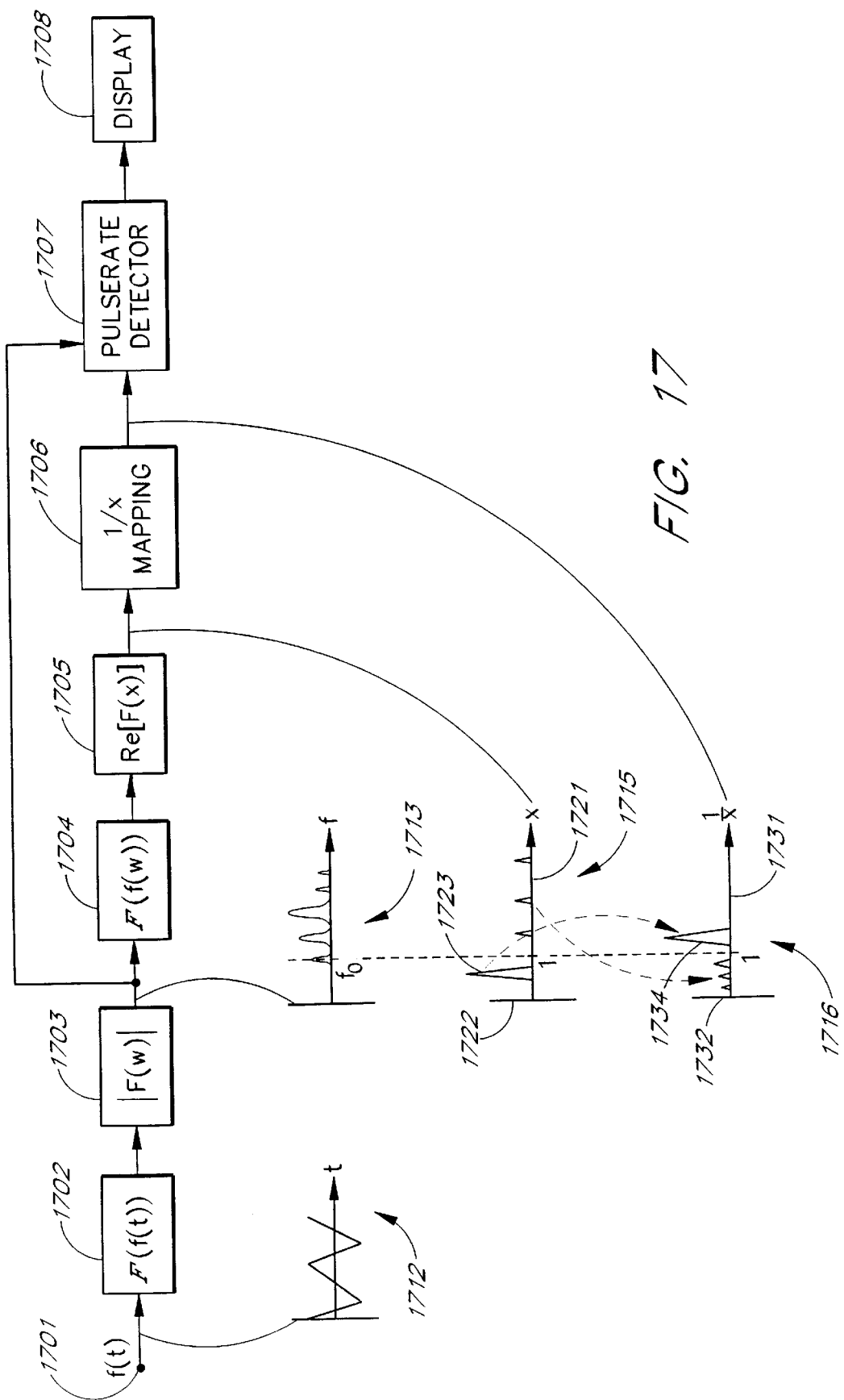
FIG. 17 is a block diagram which illustrates the signal processing used to determine pulse rate by the pleth to pulserate transform method (PPRT) in accordance with one aspect of the present invention.

In accordance with another aspect of this invention, the pulserate can be determined in the presence of FM and AM distortions by using a pleth to pulserate transform (PPRT). FIG. 17 shows a schematic of a signal processing system that implements a PPRT. In FIG. 17, a time domain plethysmographic waveform f(t) is fed into an input 1701. The signal at the input 1701 is fed into a Fourier transform block 1702 which forward transforms f(t) into the frequency domain. An output of the block 1702 is expressed mathematically as $F(\omega)=\Im[f(t)]$. The output of the block 1702 is fed into a magnitude block 1703 which finds the magnitude of the signal $F(\omega)$. An output of the magnitude block 1703, shown as a plot 1713, is fed into a second forward Fourier transform block 1704 which transforms the signal $|F(\omega)|$ into a signal G(x) where $G(x)=\Im[|F(\omega)|]$ and G(x) is a complex number. The output of the block 1704 is fed into a block 1705 which extracts the real portion of G(x). The real portion of G(x) is then fed into a 1/x mapping block 1706. An output of the mapping block 1706 is fed into a pulserate detector block 1707. A pulserate output from the detector block 1706 is sent to a display 1708.

In an alternate embodiment, the magnitude block could be replaced by a block which extracts the real portion of the waveform. Likewise, the block 1705 which extracts the real portion of G(x) could be replaced by a magnitude block which extracts |G(x)|.

One skilled in the art will recognize that the output of the magnitude block 1703 is merely the absolute value of the Fourier transform of the plethysmographic wave f(t) on a point by point basis. The graph 1713 shows this signal as a series of spectral lines of varying amplitudes. In many cases, this spectrum will be similar to that shown in FIG. 14B, and has a fundamental frequency $f_0$, and a series of harmonics $f_1$ and $f_2$ of various amplitudes. As shown in FIG. 14B, any attempt at determining pulserate merely by finding the largest spectral line will lead to erroneous results. Further, the clean waveform of FIG. 14B, showing a series of spectral peaks, will often be contaminated by AM sidebands as shown in FIG. 15. Thus the fundamental periodic nature of the heartbeat is not always readily apparent in the spectrum of plot 1713. This is the reason for the second Fourier transform in process block 1704.

The nature of the Fourier transform is to identify and quantify the periodic nature of a function. If the waveform shown in the plot 1713 were in the time domain, rather than the frequency domain, then the series of pulses (the spectral lines of the plot 1713) would correspond to a periodic train of pulses, having a fundamental frequency given by the pulse repetition frequency and modulated by the spectrum of the individual pulses. Mathematically, it does not matter that the waveform of the plot 1713 is not in the time domain. The Fourier transform can still be applied, and it will still produce a very strong spectral line corresponding to the inherent periodicity, and corresponding component strength, of the waveform.

Thus, the operation of the block 1704, in performing a forward Fourier transform on a frequency domain waveform is mathematically viable, and yields the desired data. The only unique ramification of the fact that the transformed data is already in the frequency domain rather than the time domain is the effect on the x axis. It is well known to those skilled in the art, that the forward Fourier transform maps the x axis into 1/x. This is most easily explained by noting that, normally, one would transform f(t) into F(ω). Since t=1/ω (to within a constant factor of 2π) it is clear that a 1/x mapping has occurred. In the present context, the 1/x mapping is undesirable because the data was already in the frequency domain. Thus the mapping must be undone by the process block 1706.

Once the waveform has been remapped in the process block 1707, it is a simple matter to find the desired pulserate in the process block 1707, because the pulserate will correspond to the largest spectral peak. Again, this occurs because the second Fourier transform "identifies" the dominant periodicity (e.g., the dominant string of harmonics) and collapses that periodicity into a single spectral line. The pulserate detector 1707 merely searches for the largest spectral peak and sends, to the display 1708, the frequency that corresponds to the largest peak.

In yet another embodiment, the process block 1707 looks for the existence of a spectral peak below 120 beats per minute. If a spectral peak below 120 beats per minute is found, then the frequency corresponding that peak is the pulserate. Of, on the other hand, no spectral peak below 120 beats per minute is found, then the process block 1707 finds the largest spectral peak in the original fourier spectrum that exists at the output of the Fourier transform block 1702. The pulserate is then the frequency corresponding to the largest spectral peak at the output of the Fourier transform block 1702.

In yet another embodiment, the ratio of the largest two peaks in the PPRT waveform 1716 can be used to generate a confidence factor that provides some indication of the accuracy of the computed pulserate. In a preferred embodiment, a contrast ratio is computed by dividing the magnitude of the largest peak in the PPRT waveform 1716 by the magnitude of the second largest peak in the PPRT waveform 1716. A large contrast ratio corresponds to high confidence that the computed pulserate is accurate. A contrast ratio near unity corresponds to low confidence that the computed pulserate is accurate.

Neural Network Embodiments

In yet another embodiment, much of the signal processing can be accomplished by a neural network. One skilled in the art will recognize that the signal processing associated with the removal of motion artifacts involves non-linear and linear processes. The frequency domain waveform scrubber 1260 and the time domain waveform scrubber 1242 are both linear processes. However, the calculation of α in FIG. 12 is a non-linear process, in part because it includes the ratio operation represented by the process block 1230. The calculation of pulserate, either by the rule based method, or the PPRT method both involve ratios and are thus non-linear processes as well.

Figure 19:
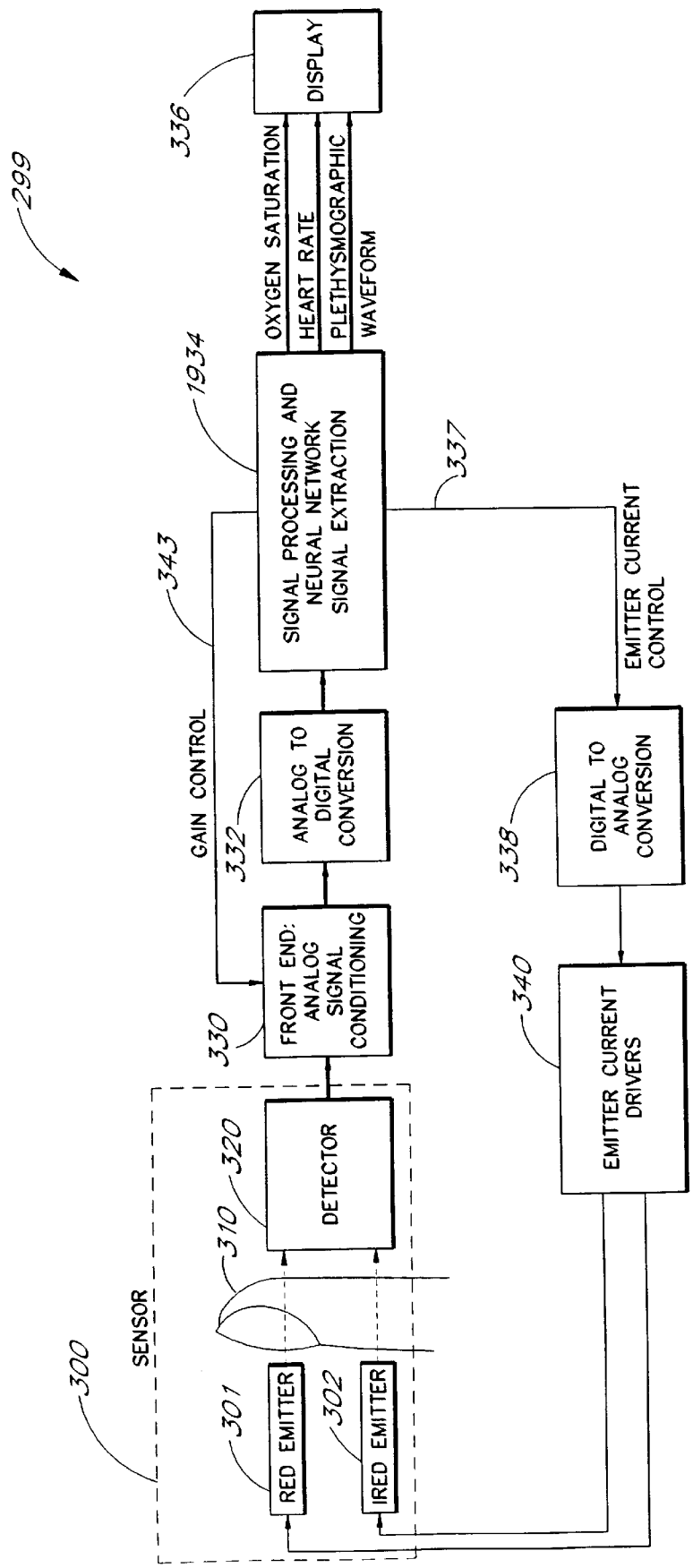
FIG. 19 illustrates a schematic diagram of a physiological monitor that uses a neural network in accordance with the teachings of one aspect of the present invention.

One skilled in the art will appreciate that other non-linear filtering processes can be used. In particular, any of these non-linear processes can be performed by a neural network as shown in FIG. 19. FIG. 19 depicts a general hardware block diagram of a pulse oximeter 299 that employs neural network processing. A sensor 300 has two light emitters 301 and 302, such as LED's. One LED 301 emitting light of red wavelengths and another LED 302 emitting light of infrared wavelengths are placed adjacent a finger 310. A photodetector 320, which produces an electrical signal corresponding to the attenuated visible and infrared light energy signals is, located near the LED's 301 and 302. The photodetector 320 is connected to front end analog signal conditioning circuitry 330.

The front end analog signal conditioning circuit 330 has outputs coupled to an analog to digital conversion circuit 332. The analog to digital conversion circuit 332 has outputs coupled to a digital signal processing and neural network signal extraction system 1934. The signal processing system 1934 provides the desired parameters as outputs for a display 336. Outputs for display are, for example, blood oxygen saturation, heart rate, and a clean plethysmographic waveform.

The signal processing system also provides an emitter current control output 337 to a digital-to-analog converter circuit 338 which provides control information for a set of light emitter drivers 340. The light emitter drivers 340 couple to the light emitters 301, 302. The signal processing system 1934 also provides a gain control output 343 for the front end analog signal conditioning circuitry 330.

Additional Embodiments

While one embodiment of a physiological monitor incorporating a processor of the present invention for determining a reference signal for use in a waveform scrubber, to remove or derive primary and secondary components from a physiological measurement has been described in the form of a pulse oximeter, it will be obvious to one skilled in the art that other types of physiological monitors may also employ the above described techniques.

In particular, one skilled in the art will recognize that in all cases, the Fourier transform disclosed above can be replaced by a Fast Fourier Transform (FFT), a Chirp-Z Transform, a wavelet transform, a discrete Fourier transform, or any other operation that produces the same or similar result.

Furthermore, the signal processing techniques described in the present invention may be used to compute the arterial and venous blood oxygen saturations of a physiological system on a continuous or nearly continuous time basis. These calculations may be performed, regardless of whether or not the physiological system undergoes voluntary motion.

Furthermore, it will be understood that transformations of measured signals other than logarithmic conversion and that the determination of a proportionality factor which allows removal or derivation of the primary or secondary signal portions for determination of a reference signal are possible. Additionally, although the proportionality factor r has been described herein as a ratio of a portion of a first signal to a portion of a second signal, a similar proportionality constant determined as a ratio of a portion of a second signal to a portion of a first signal could equally well be utilized in the processor of the present invention. In the latter case, a secondary reference signal would generally resemble n'(t)= $n_b(t)-m_a(t)$.

One skilled in the art will realize that many different types of physiological monitors may employ the teachings of the present invention. Other types of physiological monitors include, but are in not limited to, electro-cardiographs, blood pressure monitors, blood constituent monitors (other than oxygen saturation) monitors, capnographs, heart rate monitors, respiration monitors, or depth of anesthesia monitors. Additionally, monitors which measure the pressure and quantity of a substance within the body such as a breathalyzer, a drug monitor, a cholesterol monitor, a glucose monitor, a carbon dioxide monitor, a glucose monitor, or a carbon monoxide monitor may also employ the above described techniques.

Furthermore, one skilled in the art will recognize that many of the signal processing techniques, and many of the filters disclosed herein are classification techniques. Many of the classification mechanisms herein involve classification of spectral lines and ratios of various spectral lines. Other classification schemes are possible within the spirit and scope of the invention.

Furthermore, one skilled in the art will realize that the above described techniques of primary or secondary signal removal or derivation from a composite signal including both primary and secondary components can also be performed on electrocardiography (ECG) signals which are derived from positions on the body which are close and highly correlated to each other.

Furthermore, one skilled in the art will realize that the above described techniques can also be performed on signals made up of reflected energy, rather than transmitted energy. One skilled in the art will also realize that a primary or secondary portion of a measured signal of any type of energy, including but not limited to sound energy, X-ray energy, gamma ray energy, or light energy can be estimated by the techniques described above. Thus, one skilled in the art will realize that the techniques of the present invention can be applied in such monitors as those using ultrasound where a signal is transmitted through a portion of the body and reflected back from within the body back through this portion of the body. Additionally, monitors such as echo-cardiographs may also utilize the techniques of the present invention since they too rely on transmission and reflection.

While the present invention has been described in terms of a physiological monitor, one skilled in the art will realize that the signal processing techniques of the present invention can be applied in many areas, including but not limited to the processing of a physiological signal. The present invention may be applied in any situation where a signal processor comprising a detector receives a first signal which includes a first primary signal portion and a first secondary signal portion and a second signal which includes a second primary signal portion and a second secondary signal portion. Thus, the signal processor of the present invention is readily applicable to numerous signal processing areas.

What is claimed is:

1. In a signal processor for processing at least two signals $M_1$ and $M_2$, the signal $M_1$ containing a primary signal portion $S_1$ and a secondary signal portion $N_1$, the signal $M_2$ containing a primary signal portion $S_2$ and a secondary signal portion $N_2$, said signals $M_1$ and $M_2$ having the flowing relationship:

$$M_1 = S_1 + N_1$$
$$M_2 = S_2 + N_2,$$

a method comprising the steps of:
   determining a value for a coefficient c, such that an error value e, given by the relation $e = S_1 - (cM_1 - M_2)$ is partially minimized, where said coefficient c is related to a ratio of a frequency-domain representation of $M_1$ and a frequency-domain representation of $M_2$; and
   using said coefficient c in a waveform scrubber to remove some of the secondary signal portion $N_1$ from the signal $M_1$ to produce an approximation $A_1$ to said primary signal portion $S_1$, where $A_1 = cM_1 - M_2$.

2. The method of claim 1, further comprising the step of displaying said approximation $A_1$ on a display.

3. The method of claim 1, wherein said signals $M_1$ and $M_2$ are obtained from physiological signals, the method further comprising the step of processing said approximation $A_1$ to determine a physiological parameter.

4. The method of claim 1, wherein at least a portion of said primary signal portion $S_1$ is indicative of a heart plethysmograph, said method further comprising the step of calculating a pulse rate.

5. The method of claim 4, wherein said physiological parameter is arterial oxygen saturation.

6. The method of claim 4, wherein said physiological parameter is an ECG signal.

7. A physiological monitor comprising:
   a first input configured to receive a first signal $M_1$ having a primary portion, $S_1$, and a secondary portion $N_1$, said signal $M_1$ related to a physiologic parameter;
   a second input configured to receive a second signal $M_2$ having a primary portion $S_2$ and a secondary portion $N_2$, said first and said second signals $M_1$ and $M_2$ being in accordance with the following relationship:

$$M_1 = S_1 + N_1$$
$$M_2 = S_2 + N_2$$

where $S_1$ and $S_2$, and $N_1$ and $N_2$, are related by:

$$S_1 \approx r_a S_2$$

$$N_1 \approx r_v N_2$$

and where $r_a$ and $r_v$ are coefficients;

a first signal processor, said first signal processor configured to compute said $r_a$ coefficient and said $r_v$ coefficient using a transformed representation of said first signal $M_1$ and a transformed representation of said second signal $M_2$; and a waveform scrubber having a first input configured to receive said first signal $M_1$, and having a second input configured to receive said second signal $M_2$, said waveform scrubber providing an output signal corresponding to an approximation of $S_1$.

8. The physiological monitor of claim 7, further comprising a second signal processor, said second signal processor configured to compute a selected blood constituent value from at least a portion of said output signal.

9. The physiological monitor of claim 8, wherein said selected blood constituent is arterial blood oxygen saturation.

10. The physiological monitor of claim 8, wherein said selected blood constituent is venous blood oxygen saturation.

11. The physiological monitor of claim 8, wherein said selected blood constituent comprises carbon monoxide saturation.

12. The physiological monitor of claim 8, wherein said selected blood constituent value corresponds to a physiological concentration of a selected blood constituent.

13. In a signal processor for processing at least two measured signals $M_1$ and $M_2$, the signal $M_1$ having a primary signal portion $S_1$ and a secondary signal portion $N_1$, the signal $M_2$ having a primary signal portion $S_2$ and a secondary signal portion $N_2$, such that:

$$M_1 = S_1 + N_1$$

$$M_2 = S_2 + N_2$$

where $S_1$ and $S_2$, and $N_1$ and $N_2$, are related by:

$$S_1 \approx r_a S_2$$

$$N_1 \approx r_v N_2$$

and where $r_a$ and $r_v$ are coefficients, a method comprising the steps of:

determining a value for a coefficient c, such that an error value e, given by the relation $e = S_1 - (cM_1 - M_2)$ is partially minimized; and using said coefficient c in a waveform scrubber to remove some of the signal $N_1$ from the measured signal $M_1$ to produce an approximation $A_1$ to said signal $S_1$, where $A_1 = cM_1 - M_2$, and where $A_1$, $M_1$, and $M_2$ are expressed as frequency domain signals.

14. A physiological monitor comprising:

a first input configured to receive a first measured signal $M_1$ having a primary portion, $S_1$, and a secondary portion $N_1$;

a second input configured to receive a second measured signal $M_2$ having a primary portion $S_2$ and a secondary portion $N_2$, said first and said second measured signals $M_1$ and $M_2$ being in accordance with the following relationship:

$$M_1 = S_1 + N_1$$

$$M_2 = S_2 + N_2$$

where $S_1$ and $S_2$, and $N_1$ and $N_2$, are related by:

$$S_1 \approx r_a S_2$$

$$N_1 \approx r_v N_2$$

and where $r_a$ and $r_v$ are coefficients;

a first signal processor comprising a neural network configured to compute said $r_a$ coefficient and said $r_v$ coefficient using a transformed representation of said signal $M_1$ and a transformed representation of said signal $M_2$; and a waveform scrubber having a first input configured to receive said first measured signal and having a second input configured to receive said second measured signal, said waveform scrubber providing an output corresponding to an approximation of $S_1$.

* * * * *

UNITED STATES PATENT AND TRADEMARK OFFICE
CERTIFICATE OF CORRECTION

PATENT NO. : 6,067,462
DATED : May 23, 2000
INVENTOR(S) : Mohamed K. Diab and Rex McCarthy It is certified that error appears in the above-identified patent and that said Letters Patent is hereby corrected as shown below:

<u>Column 24,</u>
Line 24, change "flowing" to -- following --.

Signed and Sealed this

First Day of January, 2002

Attest:

JAMES E. ROGAN
*Attesting Officer*     *Director of the United States Patent and Trademark Office*